United States Patent
Takeuchi et al.

(10) Patent No.: US 10,471,011 B2
(45) Date of Patent: Nov. 12, 2019

(54) IN VIVO STEALTH NANOPARTICLE

(71) Applicants: Toshifumi Takeuchi, Kobe-shi, Hyogo (JP); Yukiya Kitayama, Kobe-shi, Hyogo (JP); System Instruments Co., Ltd., Hachioji-shi, Tokyo (JP)

(72) Inventors: Toshifumi Takeuchi, Kobe (JP); Yukiya Kitayama, Kobe (JP)

(73) Assignees: Toshifumi Takeuchi, Kobe-shi, Hyogo (JP); Yukiya Kitayama, Kobe-shi, Hyogo (JP); System Instruments Co., Ltd., Hachioji-shi, Tokyo (JP)

( * ) Notice: Subject to any disclaimer, the term of this patent is extended or adjusted under 35 U.S.C. 154(b) by 85 days.

(21) Appl. No.: 15/532,951

(22) PCT Filed: Dec. 4, 2015

(86) PCT No.: PCT/JP2015/006041
§ 371 (c)(1),
(2) Date: Jun. 2, 2017

(87) PCT Pub. No.: WO2016/088384
PCT Pub. Date: Jun. 9, 2016

(65) Prior Publication Data
US 2017/0319485 A1    Nov. 9, 2017

(30) Foreign Application Priority Data
Dec. 5, 2014 (JP) ................. 2014-247252

(51) Int. Cl.
| | | |
|---|---|---|
| *A61K 9/14* | (2006.01) | |
| *C08F 2/44* | (2006.01) | |
| *A61K 47/69* | (2017.01) | |
| *A61K 31/704* | (2006.01) | |
| *C08F 220/56* | (2006.01) | |
| *A61P 35/00* | (2006.01) | |
| *B82Y 5/00* | (2011.01) | |
| *A61K 9/00* | (2006.01) | |

(52) U.S. Cl.
CPC ............ *A61K 9/146* (2013.01); *A61K 31/704* (2013.01); *A61K 47/6933* (2017.08); *A61P 35/00* (2018.01); *C08F 2/44* (2013.01); *C08F 220/56* (2013.01); *A61K 9/0019* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 2009/0110601 A1 | 4/2009 | Levi et al. | |
| 2011/0160392 A1* | 6/2011 | Chang | C08F 220/38 524/608 |
| 2013/0102063 A1 | 4/2013 | Levi et al. | |
| 2015/0299366 A1* | 10/2015 | Zhang | C08F 2/38 428/402 |

FOREIGN PATENT DOCUMENTS

| | | | | |
|---|---|---|---|---|
| WO | WO 2009/083975 A2 | 7/2009 | | |
| WO | WO-2013124068 A1 * | 8/2013 | ............... | C09K 8/28 |
| WO | WO-2014079367 A1 * | 5/2014 | ............... | C08F 2/38 |

OTHER PUBLICATIONS

Tan et al., Analytical Chemistry, 80: 863-892 (Year: 2008).*
Knauer, Application Note, pp. 1-8, downloaded from http://www.knauer.net/fileadmin/user_upload/produkte/files/ Dokumente/application_notes/VBS0021N_Determination_of_Biocompatible_Polymer_building_Monomers.pdf, Sep. 16, 2017 (Year: 2012).*
Tan et al., Chemistry of Materials, 20: 118-127 (Year: 2008).*
Liu et al., Scientific Reports, 4: 5487 pp. 1-6 (Year: 2014).*
Balmert, S.C. et al. 2012 "Biomimetic Delivery with Micro- and Nanoparticles" *Advanced Materials* 24: 3757-3778.
Hu, C-M. J. et al. 2014 "Polymeric nanotherapeutics: clinical development and advances in stealth functionalization strategies" *Nanoscale* 6: 65-75.
Mikiharu Kamachi and Takeshi Endo, "Radical Polymerization Handbook" (1999) NTS Inc.
European Search Report in counterpart European Application No. 15865296.6, dated Jul. 13, 2018.
Verrecchia et al. 1995 "Non-stealth (poly(lactic acid/albumin)) and stealth (poly(lactic acid-polyethylene glycol)) nanoparticles as injectable drug carriers" Journal of Controlled Release 36: 49-61.

* cited by examiner

*Primary Examiner* — Melissa L Fisher
(74) *Attorney, Agent, or Firm* — Knobbe Martens Olson & Bear, LLP

(57) ABSTRACT

Provided is a molecular imprint polymer that is capable of acquiring stealth properties through a new mechanism. The molecular imprint polymer according to the present invention, which has a plasma protein recognition sites molecularly imprinted by a plasma protein thereon and contains a constituent derived from a biocompatible monomer, is an in vivo stealth nanoparticle to be used in intravascular delivery. As the plasma protein, albumin is preferred. When carrying a drug thereon, the in vivo stealth nanoparticle according to the present invention is usable as a drug for drug delivery system.

8 Claims, 13 Drawing Sheets

(a)

(b)

IN VIVO STEALTH NANOPARTICLE

TECHNICAL FIELD

The present invention relates to an in vivo stealth nanoparticle. More specifically, the present invention relates to a nanoparticle to be used in intravascular delivery, which is capable of acquiring stealth properties.

BACKGROUND ART

Drug delivery systems using nanoparticle-based therapeutic and diagnostic agents have been developed for the treatment and diagnosis of various diseases including cancers. One of the properties commonly given to nanoparticles applied to the drug delivery system is stealth property (immune response evasion capacity in the blood, that is, retention in the blood). The means for imparting stealth property to nanoparticles is a surface modification. For example, it is known to coat nanoparticles with various polymers such as polyethylene glycol for exerting an effect of preventing opsonin adsorption or aggregation. It is also known to coat nanoparticles with a self-marker CD47 protein for the purpose of inhibiting phagocytosis (Non-Patent Document 1 and Non-Patent Document 2).

Meanwhile, a molecular imprinting method (MI method) is known as an artificial receptor synthesis method capable of specifically recognizing a target molecule. The MI method is a method of artificially constructing a binding site having selectivity for a target molecule in a material with use of a recognition object molecule (a target molecule) as a template. The polymer synthesized using the MI method is called a molecularly imprinted polymer (MIP). The MIP is constructed by radical polymerization of a template molecule (a target molecule or a derivative thereof) and a functional monomer (a molecule having a site interacting specifically with a template molecule and a polymerizable functional group) together with a crosslinking agent, followed by removal of the template molecule from within the polymer (Non-Patent Document 3).

PRIOR ART DOCUMENTS

Non-Patent Documents

Non-Patent Document 1: Advanced Materials, 2012 Jul. 24; 24(28): 3757-3778.
Non-Patent Document 2: Nanoscale, 2014 Jan. 7; 6(1): 65-75.
Non-Patent Document 3: Supervised by Mikiharu Kamachi and Takeshi Endo, "Radical Polymerization Handbook" (1999) NTS Inc.

SUMMARY OF THE INVENTION

Problem to be Solved by the Invention

Conventionally, nanoparticles for drug delivery systems have adopted a means of surface modification of nanoparticles by molecules involved in the exertion of stealth property in order to achieve the purpose of imparting stealth property. In other words, it was common sense that nanoparticles for a drug delivery system are manufactured in a form to which a desired stealth property is given at a stage before being injected into the body.

On the other hand, any molecularly imprinted polymer showing stealth property is not known.

In view of such a situation, an object of the present invention is to provide a molecularly imprinted polymer capable of acquiring stealth properties through a novel mechanism.

Means for Solving the Problem

The present invention encompasses the following inventions in order to solve the above problem.

(1) The present invention is directed to an in vivo stealth nanoparticle. The in vivo stealth nanoparticle is a molecularly imprinted polymer which has a plasma protein recognition sites molecularly imprinted by a plasma protein thereon and contains a constituent derived from a biocompatible monomer. The in vivo stealth nanoparticle of the present invention is used in intravascular delivery.

With this constitution, stealth property (in vivo stealth property) can be acquired as a result of binding the plasma protein present in the blood vessel to the recognition site after being administered into the blood vessel.

(2) In the in vivo stealth nanoparticle of the above (1), the plasma protein may be albumin.

With this constitution, it is possible to acquire stealth properties efficiently by utilizing albumin which occupies most of the plasma protein for acquiring stealth properties.

(3) In the in vivo stealth nanoparticle of the above (1) or (2), the biocompatible monomer may be a zwitterionic compound.

With this constitution, when a drug is loaded on the in vivo stealth nanoparticle of the present invention, the drug releasing property in the body becomes favorable. Furthermore, it is easy to control the particle diameter to be smaller while maintaining the dispersion stability in blood.

(4) The in vivo stealth nanoparticle according to any one of the above (1) to (3) may have an average particle diameter of 10 nm or more and 100 nm or less.

With this constitution, EPR (enhanced permeability and retention) effect is easy to be developed, and the stealth property is easy to be ensured by molecular imprinting. The average particle diameter in the present invention means an arithmetic average diameter in a particle size distribution measured by a dynamic light scattering method.

(5) The in vivo stealth nanoparticle according to any one of the above (1) to (4) may further contain a signal group.

With this constitution, the nanoparticle can be traced using a means for detecting a signal group, from outside the living body to which the in vivo stealth nanoparticle has been administered.

(6) The in vivo stealth nanoparticle according to any one of the above (1) to (5) may be loaded with a drug component.

With this constitution, the in vivo stealth nanoparticle can be used as a drug for drug delivery systems.

(7) In the in vivo stealth nanoparticle according to the above (6), the drug component may be contained in the molecularly imprinted polymer as a constituent derived from a drug monomer in which a polymerizable functional group is covalently bonded to the drug.

With this constitution, it becomes easy to carry a drug that secures an in vivo stealth acquisition performance.

Advantages of the Invention

According to the present invention, there is provided a molecularly imprinted polymer capable of acquiring stealth properties through a new mechanism of binding a plasma protein present in a blood vessel to a recognition site after being administered intravascularly.

MODE FOR CARRYING OUT THE INVENTION

[1. In Vivo Stealth Nanoparticles]

Figure 1:
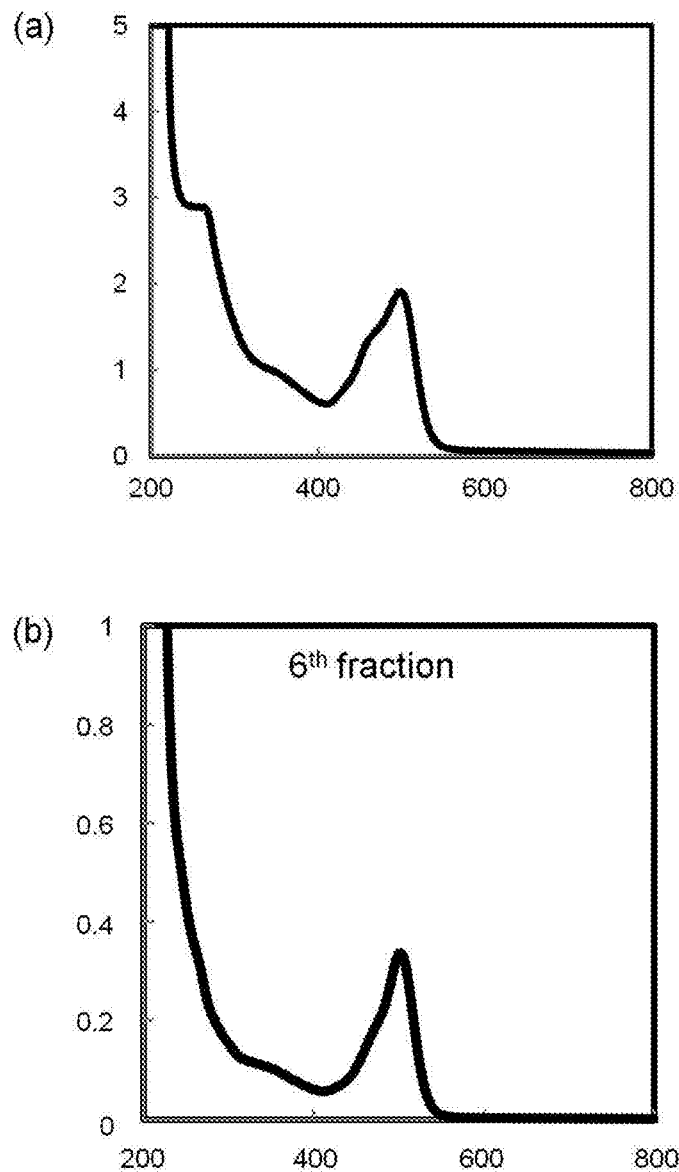
FIG. 1 shows the UV-vis spectrum before purification (a) and the UV-vis spectrum after purification (b) of the fluorescent HSA-recognizing nanoparticles [HSA]MIP-NGs obtained in Example 1.

The in vivo stealth nanoparticle of the present invention is a molecularly imprinted polymer used for intravascular delivery. The molecularly imprinted polymer is a synthetic polymer having a binding sites (a target molecule recognition sites) that is selective for the target molecule. Such a molecularly imprinted polymer is synthesized by a molecular imprinting method which is one of the template polymerization methods. The molecular imprinting method is a method of artificially constructing a binding sites (a target molecule recognition sites) having selectivity for its target molecule in a polymer, wherein the target molecule is used as a template.

[1-1. Target Molecule]

The target molecule to be recognized at the target molecule recognition site by the in vivo stealth nanoparticle of the present invention is a plasma protein. When the in vivo stealth nanoparticle of the present invention is administered intravascularly, the stealth property can be acquired by the binding of the plasma protein in the blood to the target molecule recognition site of the molecularly imprinted polymer. As the plasma protein, there can be exemplified albumin, γ-globulin, fibrinogen, transferrin, ceruloplasmin, carcinoembryonic antigen, and the like, among which albumin, which is the most common in the plasma, is preferred. In this case, the stealth property of the in vivo stealth nanoparticles in the blood can be secured more efficiently. The plasma protein may be derived from humans and non-human animals. Non-human animals include vertebrates including mammals such as mice, rats, monkeys, dogs, cats, cattle, horses, pigs, hamsters, rabbits, goats, etc.

[1-2. Constituent Material of Molecularly Imprinted Polymer]

The molecularly imprinted polymer constituting the in vivo stealth nanoparticle of the present invention is a cross-linked polymer containing at least a component derived from each of a functional monomer and a biocompatible monomer.

The functional monomer means a molecule having both a functional group capable of binding to a plasma protein as a target molecule and a polymerizable functional group. The mode of binding to the plasma proteins may be covalently bonded or non-covalently bonded. The non-covalent bonds include hydrogen bonds, ionic bonds, electrostatic interactions, van der Waals interactions, hydrophobic interactions, and the like.

Examples of the functional group capable of binding to the plasma protein include an acidic functional group (e.g. sulfonic acid group, carboxyl group, etc.), a basic functional group [e.g. amino group, cyclic secondary amino group (for example, pyrrolidyl group, piperidyl group), pyridyl group, imidazole group, guanidine group, etc.], a carbamoyl group, a hydroxyl group, an aldehyde group, and the like. Examples of the polymerizable functional group include a vinyl group and a (meth)acrylic group (the same applies to other monomers). Specific examples of the functional monomer include pyrrolidyl acrylate, acrylic acid, methacrylic acid, acrylamide, 2-(dimethylamino)ethyl methacrylate, hydroxyethyl methacrylate, and the like. The functional monomer can be appropriately selected depending on the plasma protein to be used as a template.

The biocompatible monomer refers to a monomer that can constitute a biocompatible polymer. The biocompatible polymer is preferably a hydrophilic polymer and includes a zwitterionic polymer and a nonionic polymer. Biocompatibility refers to a property that does not induce adhesion of a biological substance. By including a component derived from such a monomer, the molecularly imprinted polymer per se can be provided with favorable retention in the blood.

The zwitterionic monomer that can constitute a zwitterionic polymer contains both an anionic group derived from an acidic functional group (e.g. a phosphate group, a sulfate group, a carboxyl group) and a cationic group derived from a basic functional group (e.g. a primary amino group, a secondary amino group, a tertiary amino group, a quaternary ammonium group) in one molecule. For example, phosphobetaine, sulfobetaine, carboxybetaine, and the like can be mentioned as the zwitterionic monomer.

More specifically, examples of the phosphobetaine include a molecule having a phosphorylcholine group in the side chain, preferably such as 2-methacryloyloxyethyl phosphorylcholine (MPC) or the like.

Examples of the sulfobetaine include N,N-dimethyl-N-(3-sulfopropyl)-3'-methacryloylaminopropanaminium inner salt (SPB), N,N-dimethyl-N-(4-sulfobutyl)-3'-methacryloylaminopropanaminium inner salt (SBB), and the like.

Examples of the carboxybetaine include N,N-dimethyl-N-(1-carboxymethyl)-2'-methacryloyloxyethanaminium inner salt (CMB), N,N-dimethyl-N-(2-carboxyethyl)-2'-methacryloyloxyethanaminium inner salt (CEB), and the like.

To have a component derived from a zwitterionic monomer is preferable in terms of drug-releasing property when a drug is loaded on a molecularly imprinted polymer, and is also preferable in terms of easy control of the particle diameter while maintaining the dispersion stability in the blood.

As the nonionic polymer, a polyether polymer such as poly(ethylene glycol)(PEG) can be mentioned. When a nonionic polymer such as PEG is contained in a molecularly imprinted polymer, blood dispersion stability due to molecular exclusion effect can be obtained.

The component derived from a biocompatible monomer can be contained in an amount of, for example, more than 0% and 50% or less (the amount expressed in percent is on a molar basis), preferably 1% or more and 30% or less, more preferably 2% or more and 20% or less, of the molecularly imprinted polymer. When the content of the biocompatible monomer-derived component is not more than the above upper limit value, the plasma protein recognition sites molecularly imprinted by a plasma protein thereon can be maintained favorably, and when the content of the biocompatible monomer-derived component is not less than the lower limit value, it is possible to obtain favorable retention in the blood.

In addition to the above, the molecularly imprinted polymer may have a constituent derived from a water-soluble monomer. In this case, the water-soluble monomer means a monomer capable of constituting an external stimulus-responsive polymer such as a thermoresponsive polymer having a lower critical solution temperature (LCST), a pH-responsive polymer, or the like.

The thermoresponsive polymers with LCST include poly(N-isopropylacrylamide) (PNIPAM), poly(N,N-diethylacrylamide), poly(vinyl methyl ether), polyethylene oxide (PEO), polymer containing a polyethylene oxide side chain (for example, poly(diethylene glycol methacrylate), poly(triethylene glycol methacrylate), poly(oligoethylene glycol methacrylate)), polyvinyl acetate saponification product, methyl cellulose, hydroxypropyl cellulose and the like. By having such a constituent, the molecularly imprinted polymer exhibits hydrophilicity in a low temperature range, while exhibiting hydrophobicity due to a temperature change to LCST or more, resulting in being easily taken into cells.

As the pH-responsive polymer, there are exemplified an anionic polymer exhibiting hydrophilicity in an alkaline range (for example, poly(meth)acrylic acid) and a cationic polymer exhibiting hydrophilicity in an acidic range (for example, polyacrylamide, methacryloxyethyltrimethyl ammonium chloride modified polymer (MADQUAT)) and the like.

In addition to the above, the molecularly imprinted polymer may have a constituent derived from a signal group-containing monomer. The signal group may be any detectable functional group, and can be appropriately selected from, for example, a fluorescent group, a radioactive element-containing group, a magnetic group and the like by a person skilled in the art.

Examples of the fluorescent group include groups derived from fluorescein dyes, cyanine dyes (e.g. indocyanine dyes, etc.), rhodamine dyes, quantum dots, and the like. The fluorescent group is preferably a near infrared fluorescent group having high permeability to living bodies. The radioactive element-containing groups include groups derived from sugars, amino acids, nucleic acids and the like, which are labeled with radioactive isotopes such as $^{18}$F. Examples of the magnetic group include those having a magnetic substance such as ferrichrome, those found in ferrite nanoparticles and nanomagnetic particles, and the like.

[1-3. Drug Loading]

The in vivo stealth nanoparticle of the present invention can be used as a carrier for a drug or the like, and can carry drugs such as anticancer agents, genes, contrast agents, fluorescent probes, and proteins such as enzymes.

As the anti-cancer drug, any anti-cancer drugs generally used for cancer treatment may be used. Specific examples thereof include taxane drugs, platinum preparations, nitrosourea drugs, nitrogen mustard drugs, triazine drugs, anthracycline drugs, *vinca* alkaloid drugs, epipodophyllotoxin drugs, camptothecin drugs, and fluorinated pyrimidine drugs. The taxane drugs include taxol, taxotere, paclitaxel, docetaxel, and the like. As the platinum preparations, there are exemplified cisplatin, carboplatin and the like. Examples of the nitrosourea drugs include carmustine, lomustine, and the like. Examples of the nitrogen mustard drugs include cyclophosphamide and the like. Examples of triazine drugs include dacarbazine and the like. The anthracycline drugs include doxorubicin and the like. The *vinca* alkaloid drugs include vincristine, vinblastine and the like. Examples of the epipodophyllotoxin drugs include etoposide and the like. Examples of the camptothecin drugs include irinotecan and the like. Examples of the fluorinated pyrimidine drugs include 5-fluorouracil and tegafur.

The drug may be loaded by a covalent bond in the in vivo stealth nanoparticle. Specifically, the drug can be loaded by incorporating a constituent derived from a drug monomer as a constituent of a molecularly imprinted polymer. The drug monomer has a structure in which the drug is covalently bonded to a polymerizable functional group.

The drug monomer can be obtained by reacting a desired drug with a monomer having a polymerizable functional group (a polymerizable monomer).

In this case, as a reactive group on the drug side, a group which does not hinder the expression of the efficacy of the drug itself is appropriately selected by a person skilled in the art. In the case where two or more corresponding reactive groups are present in one molecule of a drug, a person skilled in the art can appropriately determine one suitable reactive group in view of the in vivo degradability (that is, drug-releasing property) of the covalent bond composed of the reactive group and the polymerizable monomer.

The reactive group on the polymerizable monomer side, which is a group other than the polymerizable functional group and capable of reacting with the reactive group on the drug side, is appropriately selected by a person skilled in the art. Therefore, although the polymerizable monomer to be reacted with the drug is not particularly limited, examples thereof include monomers having a carboxyl group, such as acrylic acid and methacrylic acid; monomers having a hydroxyl group, such as hydroxyalkyl acrylate and hydroxyalkyl methacrylate; methylol acrylate, methylol methacrylate; monomers having a vinyl group, such as allyl acrylate and allyl methacrylate; monomers having a glycidyl group, such as glycidyl acrylate and glycidyl methacrylate; monomers having an amino group; and monomers having a sulfonic acid group.

Incidentally, the reactive group on the drug side and the reactive group on the polymerizable monomer side may be directly bonded by condensation or the like, or may be bonded via a linking group which may be appropriately selected from the molecular design of the drug monomer by a person skilled in the art.

[1-4. Particle Diameter]

The average particle diameter of the in vivo stealth nanoparticles of the present invention may be 10 nm or more and 100 nm or less, preferably 40 nm or more and 60 nm or less, more preferably 40 nm or more and 50 nm or less. When the average particle diameter is equal to or less than the above upper limit value, EPR (enhanced permeability and retention) effect is easily exhibited and when the average particle diameter is not less than the lower limit value, it is easy to secure the specific surface area of the molecularly imprinted polymer and to acquire the stealth property.

The average particle diameter means an arithmetic average diameter in the particle size distribution measured by the dynamic light scattering method. The dynamic light scattering method is a method of deriving the particle size (particle diameter) based on the fluctuation of the scattered light intensity depending on the Brownian motion of the particles detected when a laser beam is irradiated to a solution in which particles are dispersed and then the scattered light change is measured. Particle diameter measuring apparatuses based on the dynamic light scattering method are commercially available from various companies (for example, Otsuka Electronics Co., Ltd., Sysmex Corporation, Beckmann Coulter, Inc., etc.), and can be used suitably for measuring the average particle diameter of the in vivo stealth nanoparticles of the present invention.

[2. Production of In Vivo Stealth Nanoparticles]

The in vivo stealth nanoparticles of the present invention are synthesized by a molecular imprinting method. Specifically, a target molecule, plasma protein, a derivative thereof, or a similar compound is used as a template molecule, and this template molecule is made to coexist in the radical polymerization reaction. With the coexistence of the template molecule, a molecule recognition sites that interact complementarily to the template molecule are constructed together with the synthesis of the organic polymer. Details of the method of synthesizing the molecularly imprinted polymer can be appropriately decided by a person skilled in the art with reference to the description of, for example, the reference "Komiyama, M., Takeuchi. T., Mukawa, T., Asanuma, H. "Molecular Imprinting", WILEY-VCH, Weinheim, 2002".

The polymerization reaction system in which the template molecule coexists may include at least a functional monomer, a biocompatible monomer, and a crosslinking agent. Besides this, the polymerization reaction system may further contain at least one of the above-mentioned water-soluble monomer (that is, a monomer capable of constituting an external stimulus-responsive polymer), a signal group-containing monomer, and a drug monomer. Such a system may further contain at least one of a polymerization initiator and a polymerization accelerator. Instead of each monomer mentioned above, oligomers and/or polymers of such monomers may be contained.

Specific examples of each monomer include various compounds mentioned in the item 1-2 (constituent material of molecularly imprinted polymer) and item 1-3 (drug loading).

As the crosslinking agent, it is preferable to use a molecule having at least two polymerizable functional groups (such as vinyl groups) in the molecule, and examples thereof include ethylene glycol dimethyl acrylate, N,N'-methylenebisacrylamide, divinylbenzene, etc.

Examples of the polymerization initiator include peroxides such as ammonium persulfate and potassium persulfate, azo polymerization initiators such as azobisisobutyronitrile and 2,2'-azobis(2-methylpropionamidine) dihydrochloride.

Examples of the polymerization accelerator include N,N,N',N'-tetramethylethylenediamine and the like.

As the solvent, an aqueous solvent such as a buffer solution is preferably used from the viewpoint of suppressing denaturation of the template molecule.

In the molecular imprinting method, it is possible to start the polymerization reaction by allowing all of the above components to coexist simultaneously. Alternatively, a template molecule/functional monomer complex may be formed in advance, and then the template molecule/functional monomer complex may be subjected to a polymerization reaction together with a biocompatible monomer and a crosslinking agent.

In this way, an organic polymer which memorizes the shape of the template molecule and the arrangement of the interaction points. The bonding mode between the template molecule and the component derived from the functional monomer in the obtained organic polymer may be a covalent bond or a noncovalent bond as long as it is cleavable. When the bonding mode is a noncovalent bond, it is not always necessary to form a template molecule/functional monomer complex in advance, and thus such a noncovalent bond is preferable in that its cleavage can be easily carried out.

Incidentally, as a polymerization method for obtaining fine particles of a molecularly imprinted polymer, there are exemplified an emulsifier-free precipitation polymerization method, a dispersion polymerization method, an emulsion polymerization method, a seeded emulsion polymerization method and the like (reference: Supervised by Mikiharu Kamachi and Takeshi Endo, "Radical Polymerization Handbook" (1999) NTS Inc.; and G. Schmid Ed. Nanoparticles. Wiley-VCH (2004)).

By removing the template molecule from the organic polymer obtained by the above polymerization reaction, an organic polymer (molecularly imprinted polymer) having a molecule recognition site interacting with a template molecule in a substrate specific manner is obtained. Removal of the template molecule can be carried out by cleaving the bond between the template molecule and the functional monomer-derived component and separating the released template molecule from the molecularly imprinted polymer.

The cleavage of the template molecule can be appropriately determined by a person skilled in the art based on the binding mode between the template molecule and the functional monomer-derived component. The cleavage can be carried out, for example, with 1M NaCl solution; a polar solvent (e.g. alcohols such as methanol); a surfactant (e.g. sodium dodecyl sulfate (SDS), sodium dodecylbenzene sulfonate (SDBS), tetradecyltrimethylammonium bromide (TTAB), cetyltrimethylammonium bromide (CTAB), polyoxyethylene alkyl phenyl ether (Triton), fatty acid ester (Span), polyoxyethylene ether fatty acid ester (Tween)); a protein denaturing agent (e.g. tris[2-carboxyethyl] phosphine hydrochloride (TCEP), urea, glycine salt, acid, alkali); an enzyme (e.g. pepsin, trypsin, papain); or the like. The step of cleaving the noncovalent bonds may be carried out simultaneously in the separation step described later. In this case, the mobile phase (buffer solution) used in the separation step can function as an eluent of the template molecule.

The released template molecule is separated from the molecularly imprinted polymer. A person skilled in the art can appropriately select the separation method utilizing the difference between the physical properties of the released template molecule and the molecularly imprinted polymer. Preferably the released template molecule can be separated by a size exclusion chromatography.

[3. Utilization of In Vivo Stealth Nanoparticles]

The in vivo stealth nanoparticle of the present invention can be used as a pharmaceutical composition together with a pharmaceutically acceptable ingredient by carrying a drug. The pharmaceutically acceptable ingredient is a solid and/or a liquid that does not affect the target molecule recognition site of non-toxic, inactive, and in vivo stealth nanoparticles, such as sterile water, physiological saline, a stabilizer, an excipient, an antioxidant, a buffer, an antiseptic, a pH adjuster, a surfactant, a binder, and the like.

The pharmaceutical composition can be prepared in a form to be administered to the body by a method such as injection and transdermal absorption.

EXAMPLES

Hereinafter, the present invention will be specifically described with reference to Examples, but the present invention is not limited to the following Examples.

1. Synthesis of Nanoparticles [HSA]MIP-NGs and NIP-NGs 1-1. Example 1: Synthesis of Fluorescent HSA-Recognizing Nanoparticles [HSA]MIP-NGs N-Isopropylacrylamide (NIPAm) (407 mg) as a water-soluble monomer, 30.8 mg of N,N'-methylenebisacrylamide (MBAA) as a crosslinking agent, 70 mg of pyrrolidyl acrylate (PyA) as a functional monomer, 4 mg of fluorescein acrylamide (FAm) as a fluorescent monomer, 59 mg of methacryloyloxyethyl phosphorylcholine (MPC) as a biocompatible monomer, 217 mg of 2,2'-azobis(2-methylpropionamidine) dihydrochloride (V-50) as an initiator, and 13.2 mg of human serum albumin (HSA, present in 50-60% in blood) as a target protein were dissolved in 100 mL of 10 mM PBS (pH 7.4) in a Schlenk flask. The resulting solution was subjected to an emulsifier-free precipitation polymerization under a nitrogen atmosphere at 70° C. for 12 hours. Thereby, a molecularly imprinted polymer ([HSA]MIP-NGs) was synthesized using human serum albumin as a template.

Incidentally, pyrrolidyl acrylate is a monomer having the following structure and was obtained by synthesizing an intermediate N-Boc-pyrrolidyl acrylate from Boc-3-hydroxypyrrolidine and acryloyl chloride by the method described in: Inoue Y., Kuwahara A., Ohmori K., Sunayama H., Ooya T., Takeuchi T., Biosensors and Bioelectronics 48, 113-119 (2013) and then deprotecting the Boc group.

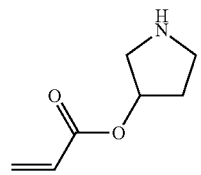

[Chem. 1]

1-2. Comparative Example 1: Synthesis of Fluorescent Reference Nanoparticles NIP-NGs The emulsifier-free precipitation polymerization was carried out in the same manner as above, except that human serum albumin was not used. Thereby, reference nanoparticles (NIP-NGs) were synthesized.

1-3. Measurement of Average Particle Diameter of Nanoparticles [HSA]MIP-NGs and NIP-NGs after Polymerization DLS measurement of the obtained nanoparticles [HSA] MIP-NGs and NIP-NGs were carried out. For the DLS measurement, a dynamic light scattering photometer (DLS) (Zetasizer manufactured by Malvern Instruments Ltd.) was used under the temperature condition set to 25° C.

As a result, the fluorescent HSA-recognizing nanoparticles [HSA]MIP-NGs had a Z-average particle diameter of 44 nm and a PDI of 0.38 nm. The fluorescent reference nanoparticles NIP-NGs had a Z-average particle diameter of 19 nm and a PDI of 0.46 nm. These values showed that stable nanoparticles were successfully obtained.

2. Purification of Nanoparticles [HSA]MIP-NGs and NIP-NGs

2-1. Purification of Fluorescent HSA-Recognizing Nanoparticles [HSA]MIP-NGs When UV-vis spectrum of the nanogel emulsion of the fluorescent HSA-recognizing nanoparticles [HSA]MIP-NGs after polymerization was measured, absorption at the wavelength of about 510 nm derived from the fluorescein group and also absorption at the wavelength of 200 to 300 nm derived from the monomer and HSA were observed.

Therefore, the nanoparticles ([HSA]MIP-NGs, NIP-NGs) were purified from the emulsion obtained by polymerization. Such purification was performed by separation using a size exclusion chromatography. Specifically, Sephadex G-50 Medium was filled in a column with an inner diameter of 1.2 cm to a height of 33 cm, and 2 mL of the obtained nanogel emulsion ([HSA]MIP-NGs or NIP-NGs) was introduced. As the eluent, 10 mM PBS buffer (pH 7.4) was used. Fractions were collected in 1.5 mL aliquots and checked for size exclusion chromatographic separation by UV-vis measurement of each fraction.

As a result of separation of the fluorescent HSA-recognizing nanoparticles [HSA]MIP-NGs, absorption at 502 nm derived from the fluorescein group was observed in the 5th to 10th fractions, and absorption at 260 nm derived from HSA was also observed in the 7th to 10th fractions among the fractions. Furthermore, in the 13th to 25th fractions, absorption at 241 nm derived from the monomer was observed.

Then, the sixth fraction in which the absorption of impurities (HSA and monomers) was not observed and the absorption at 502 nm derived from the fluorescein group was the largest was adopted as a purified product of [HSA]MIP-NGs. At this time, the solid content concentration of the fluorescent HSA-recognizing nanoparticles [HSA]MIP-NGs was measured to be 0.112 wt %. FIG. 1(a) shows the UV-vis spectrum of the polymer before purification, and FIG. 1(b) shows the UV-vis spectrum of the 6th fraction after purification. In FIG. 1, the horizontal axis represents a wavelength (nm) and the vertical axis represents a relative intensity.

It is considered that the fluorescent HSA-recognizing nanoparticles [HSA]MIP-NGs are able to be completely separated from the HSA by using a chromatography medium with a higher theoretical plate number on the higher molecular weight.

2-2. Purification of Fluorescent Reference Nanoparticles NIP-NGs

For the fluorescent reference nanoparticles NIP-NGs, fractionation was similarly carried out to obtain a purified product. At this time, the solid content concentration of NIP-NGs was 0.106 wt %.

Figure 2:
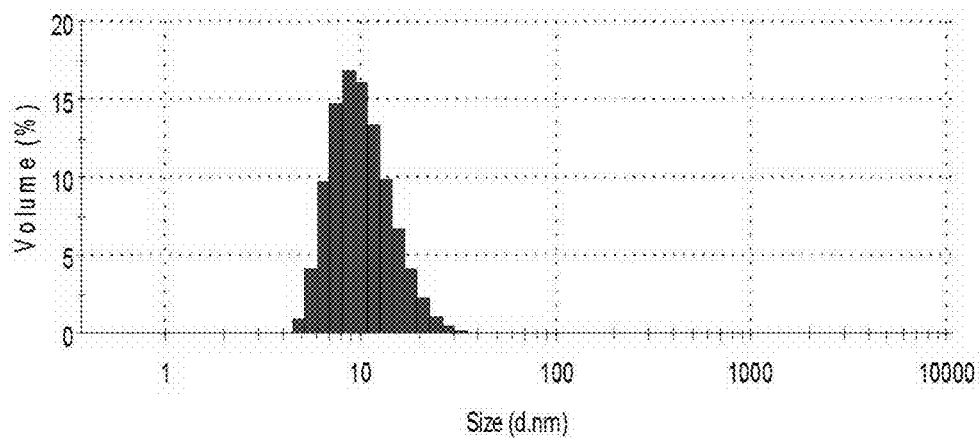
FIG. 2 shows the particle size distribution obtained by DLS of the fluorescent HSA-recognizing nanoparticles [HSA]MIP-NGs of Example 1.

2-3. Measurement of Average Particle Diameter of Fluorescent HSA-Recognizing Nanoparticles [HSA]MIP-NGs after Purification The average particle diameter of purified fluorescent HSA-recognizing nanoparticles [HSA]MIP-NGs was measured in the same manner as before purification. As a result, the average particle diameter of the fluorescent HSA-recognizing nanoparticles [HSA]MIP-NGs was 23 nm, and the PDI was 0.45. FIG. 2 shows the particle size distribution of fluorescent HSA-recognizing nanoparticles [HSA]MIP-NGs obtained by DLS.

3. Fluorescence Measurement of Nanoparticles [HSA]MIP-NGs and NIP-NGs

Purified fluorescent HSA-recognizing nanoparticles [HSA]MIP-NGs were diluted to 1/1000 (solvent: 10 mM PBS buffer (pH 7.4)) and fluorescence measurement was carried out.

For the fluorescent HSA-recognizing nanoparticles [HSA]MIP-NGs, the excitation spectrum at the fluorescence wavelength of 530 nm was measured to show the maximum absorption around 500 nm. Therefore, the fluorescence spectrum of the fluorescent HSA-recognizing nanoparticles [HSA]MIP-NGs was measured at an excitation wavelength of 500 nm and 25° C. to show the maximum absorption at 526 nm.

Likewise, for the fluorescent reference nanoparticles NIP-NGs, the fluorescence spectrum was measured to show the same maximum absorption.

Therefore, it became clear that it is possible to observe nanoparticles [HSA]MIP-NGs and NIP-NGs under a fluorescence microscope.

4. Fluorescence Depolarization Measurement of Fluorescent HSA-Recognizing Nanoparticles [HSA]MIP-NGs Purified fluorescent HSA-recognizing nanoparticles [HSA]MIP-NGs were diluted to 1/1000 (solvent: 10 mM PBS buffer (pH 7.4)). A polarizing plate of 0° or 90° was inserted on the light source side and a polarizing plate of 0° or 90° was inserted on the detector side, and then the fluorescence was measured. Specifically, the fluorescence intensity ($I_{00}$) in the case of 0° on the light source side and 0° on the detector side was measured; the fluorescence intensity ($I_{09}$) in the case of 0° on the light source side and 90° on the detector side was measured; the fluorescence intensity ($I_{90}$) in the case of 90° on the light source side and 0° on the detector side was measured; and the fluorescence intensity ($I_{99}$) in the case of 90° on the light source side and 90° on the detector side was measured. The maximum wavelength was 526 nm.

Fluorescein acrylamide which is a fluorescent monomer before polymerization was also subjected to fluorescence measurement in the same manner. The maximum wavelength was 510 nm.

For each of fluorescent HSA-recognizing nanoparticles [HSA]MIP-NGs and fluorescein acrylamide, the fluorescence intensity at the maximum wavelength was introduced into the following formula and the anisotropy was calculated (Table 1).

$$A = \frac{I_{00} \times I_{99} - I_{09} \times I_{90}}{I_{00} \times I_{99} + 2 \times (I_{09} \times I_{90})} \quad [\text{Math. 1}]$$

TABLE 1

|  | Fluorescein acrylamide | MIP-NGs |
|---|---|---|
| $I_{00}$ | 838.9 | 209.3 |
| $I_{09}$ | 528.2 | 78.22 |
| $I_{90}$ | 447 | 64.43 |
| $I_{99}$ | 293.8 | 42.66 |
| A | 0.0144 | 0.205 |

As shown in Table 1, the anisotropy value A of the fluorescent HSA-recognizing nanoparticles [HSA]MIP-NGs was calculated to be 0.205, whereas the anisotropy value A of the fluorescein acrylamide was calculated to be 0.0144. Thus, the anisotropy value A of the fluorescent HSA-recognizing nanoparticles [HSA]MIP-NGs is clearly larger than in the case of the fluorescein acrylamide. This result clearly shows that depolarization due to Brownian motion was suppressed because the size was increased by incorporation of the fluorescent molecules into the nanogel particles.

5. Evaluation of Target Molecule Recognition Ability of Fluorescent HSA-Recognizing Nanoparticles Utilizing Surface Plasmon Resonance 5-1. Preparation of HSA-Immobilized Gold Substrate First, a gold substrate was washed with water and ethanol and then treated with UV-O3. Immediately thereafter, the gold substrate was immersed in 5 mL of 11-mercaptoundecanoic acid (1 mM, ethanol) and incubated at 25° C. for 24 hours to obtain a self-assembled monolayer (SAM) film of 11-mercaptoundecanoic acid (SAM film forming step).

Next, the SAM film-formed substrate thus obtained was washed with ethanol and immersed in 0.3 mL of a solution in which N-ethyl-(dimethylaminopropyl)carbodiimide (EDC) (100 mg/mL) and N-hydroxysuccinimide (NHS)(100 mg/mL) were dissolved, at room temperature for 30 minutes. As a result, the carboxylic acid was activated by NHS modification (activation step).

Finally, the substrate on which the carboxylic acid was activated was incubated (25° C., 1.5 hours) in 10 mM PBS buffer (pH 7.4) in which HSA (1 mg/mL) was dissolved. As a result, an HSA-immobilized gold substrate was prepared (HSA immobilization step).

The treatment of each step was confirmed by X-ray photoelectron spectroscopy (XPS) measurement.

As a result of the XPS measurement of the substrate obtained by the SAM film forming step, the trajectory derived from the S2p orbital was clearly confirmed. Therefore, it was found that the surface of the substrate was modified with the carboxyl group.

As a result of the XPS measurement of the substrate obtained by the activation step, a peak derived from the N1s orbital appeared. Therefore, it was suggested that the NHS end where the carboxyl group was activated was present on the surface. (It is thought that the carbodiimide is inactivated due to its instability).

As a result of XPS measurement of the substrate obtained by the HSA-immobilizing process, the peak of N1s orbital became extremely larger (considered to be derived from the amide bond). Furthermore, a peak attributed to the carbonyl clearly appeared also in the C1s orbital. Therefore, modification with HSA was found to be successful.

5-2. Confirmation of Adsorption Behavior of Nanoparticles [HSA]MIP-NGs and NIP-NGs Using HSA-Immobilized Gold Substrate Using a surface plasmon resonance (SPR) sensor device (Biacore Q, manufactured by Biacore Co. Ltd.), the adsorption behavior of the fluorescent HSA-recognizing nanoparticles [HSA]MIP-NGs on the HSA-immobilized substrate was confirmed. The measurement was carried out using 10 mM PBS (pH 7.4) as a running buffer under the condition of a temperature of 25° C., a flow rate of 20 μL/min, and an injection volume of 20 μL. The fluorescent HSA-recognizing nanoparticles [HSA]MIP-NGs were dispersed in 10 mM PBS buffer (pH 7.4), and the concentrations were varied at 100, 200, 400, 800, and 1600 ng/mL for measurement.

Measurement was also carried out for the fluorescent reference nanoparticles NIP-NGs in the same procedure.

Figure 3:
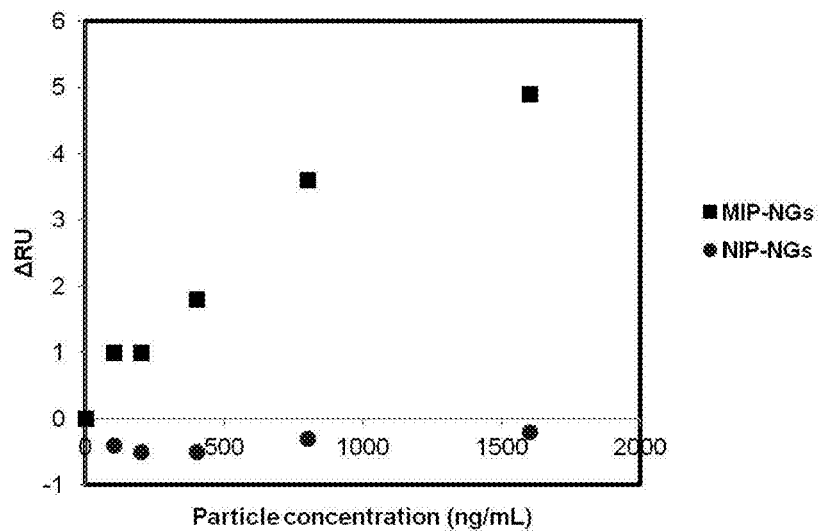
FIG. 3 shows the variation of the RU value and the particle concentration regarding the adsorption behavior of the fluorescent HSA-recognizing nanoparticles [HSA]MIP-NGs of Example 1 and the fluorescent reference nanoparticles NIP-NGs of Comparative Example 1 on each HSA-immobilized substrate.

FIG. 3 shows the relationship between resonance unit variation (ΔRU) and particle concentration (ng/mL) on each adsorption behavior of the fluorescent HSA-recognizing nanoparticles [HSA]MIP-NGs and the fluorescent reference nanoparticles NIP-NGs to the HSA-immobilized substrate.

As shown in FIG. 3, the adsorption amount of the fluorescent HSA-recognizing nanoparticles [HSA]MIP-NGs increased with the increase in the concentration, whereas no adsorption behavior as observed with the fluorescent HSA-recognizing nanoparticles [HSA]MIP-NGs was observed in the fluorescent reference nanoparticles NIP-NGs. Therefore, the fluorescent HSA-recognizing nanoparticles [HSA]MIP-NGs showed higher adsorption capacity to HSA. Experiments for examining the adsorption capacity of HSA for each of the fluorescent reference nanoparticles NIP-NGs and the fluorescent HSA-recognizing nanoparticles [HSA]MIP-NGs were carried out three times in total, and the reproducibility of the effect was confirmed.

6. Evaluation of In Vivo Retention in Blood

The tail vein of rat was injected with 10 mM PBS (pH 7.4) in which purified fluorescent HSA-recognizing nanoparticles [HSA]MIP-NGs were dispersed. Fluorescent moving images of rat ear vessels were photographed using a confocal laser microscope (manufactured by Nikon Corporation). Fluorescence intensities in arteries, veins and tissues were measured with time over a period of 10 hours.

Figure 4:
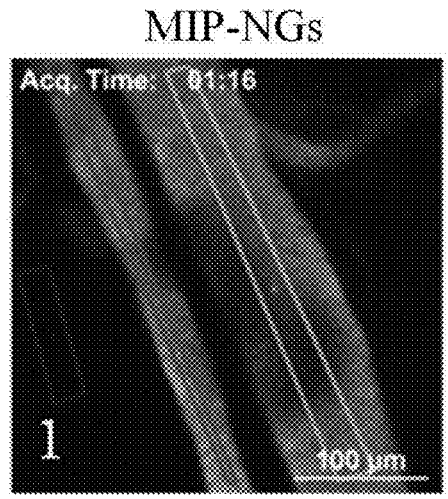
FIG. 4 is a microscopic image of blood vessels of the ear after administration of the fluorescent HSA-recognizing nanoparticles [HSA]MIP-NGs of Example 1 to a rat.
Figure 5:
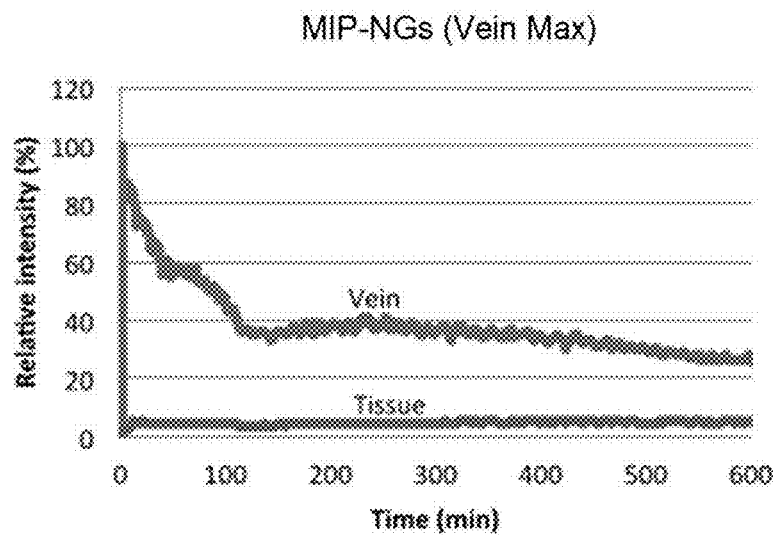
FIG. 5 shows the time course of fluorescence intensities in veins and tissues after administration of the fluorescent HSA-recognizing nanoparticles [HSA]MIP-NGs of Example 1 to a rat.

A microscopic image at an integration time of 1 hour and 16 minutes is shown in FIG. 4. In FIG. 4, the time course in the fluorescence intensity were examined at points surrounded by a square (the measurement points of tissues, arteries, and veins are shown in order from the left in the drawing). The time course in fluorescence intensities in veins and tissues is shown in FIG. 5. In FIG. 5, the horizontal axis represents a time (minutes) and the vertical axis represents a relative intensity (%).

Figure 6:
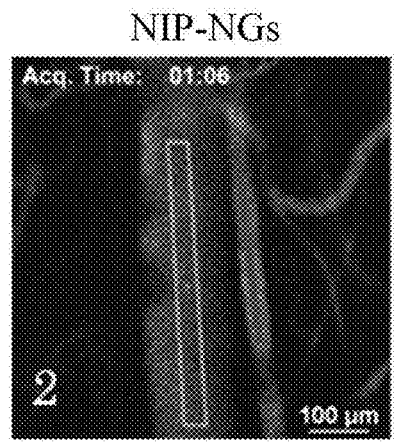
FIG. 6 is a microscopic image of blood vessels of the ear after administration of the fluorescent reference nanoparticles NIP-NGs of Comparative Example 1 to a rat.
Figure 7:
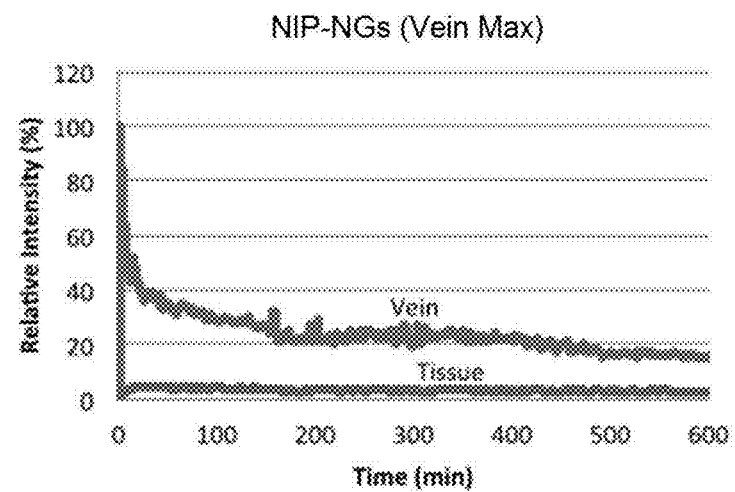
FIG. 7 shows the time course of fluorescence intensities in veins and tissues after administration of the fluorescent reference nanoparticles NIP-NGs of Comparative Example 1 to a rat.

The purified fluorescent reference nanoparticles NIP-NGs were subjected to the same procedure and the fluorescence intensity was measured with time. A microscopic image at an integration time of 1 hour and 6 minutes is shown in FIG. 6. In FIG. 6, the time course of the fluorescence intensity was examined at points surrounded by a square (the measuring points of the veins, arteries and tissues are shown in order from the left in the drawing). The time course in the fluorescence intensities in veins and tissues is shown in FIG. 7. In FIG. 7, the horizontal axis represents a time (minutes) and the vertical axis represents a relative intensity (%).

As shown in FIG. 5 and FIG. 7, the fluorescence intensities in the tissue were hardly different between the fluorescent HSA-recognizing nanoparticles [HSA]MIP-NGs and the fluorescent reference nanoparticles NIP-NGs. On the other hand, the fluorescence intensities in the veins were always higher in the fluorescent HSA-recognizing nanoparticles [HSA]MIP-NGs than in the fluorescent reference nanoparticles NIP-NGs. That is, high retention of the fluorescent HSA-recognizing nanoparticles [HSA]MIP-NGs in the blood was shown. This result suggests that the fluorescent HSA-recognizing nanoparticles [HSA]MIP-NGs are provided with stealth properties by recognizing HSA in the blood and wearing HSA.

7. Evaluation of Retention in Blood in Liver

Regarding the fluorescent HSA-recognizing nanoparticles [HSA]MIP-NGs of Example 1 and the fluorescent reference nanoparticles NIP-NGs of Comparative Example 1, the retention in the blood in liver was confirmed using a confocal laser microscope.

7-1. Experimental Procedure

Balb/c mouse (female, 4 weeks old) was used to observe the liver. First, a depilatory cream was applied to the abdomen of the mouse, and hair removal was performed. Thereafter, the skin was torn using an electronic scalpel and a scissors so that the liver can be observed from the abdomen. In order to inject the sample, a catheter was inserted into the tail vein. By introducing physiological saline with a 1 mL-Terumo syringe, no leakage was confirmed.

Focusing on the liver, 200 μL of the fluorescent HSA-recognizing nanoparticles [HSA]MIP-NGs of Example 1 was injected and observed with a confocal laser microscope. More specifically, moving images were started to be taken with a confocal laser microscope (Nikon) 5 minutes before the injection, and photographing was performed for 15 hours.

The same experimental procedure was also carried out for the fluorescent reference nanoparticles NIP-NGs of Comparative Example 1.

Figure 8:
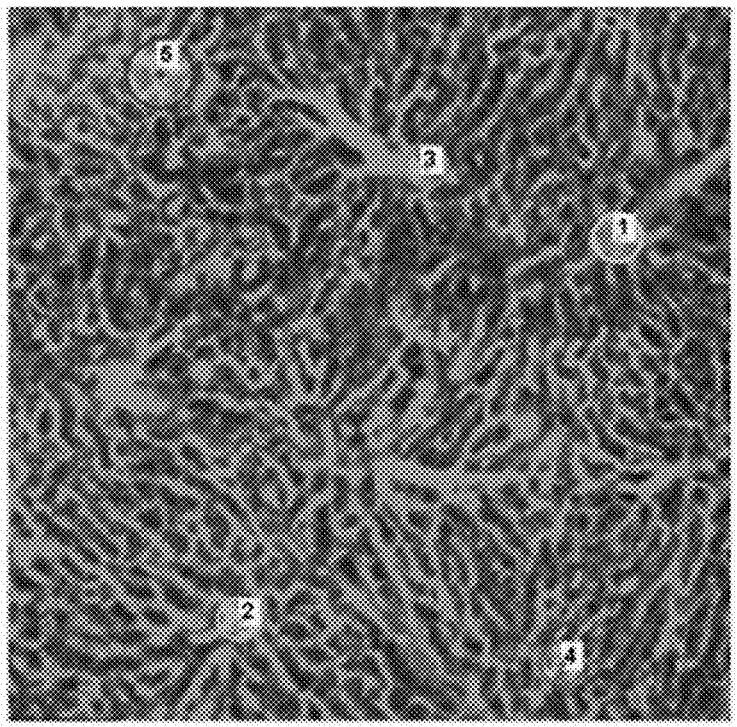
FIG. 8 shows confocal laser microscope photographs taken 10 minutes (a) and 14 hours (b) after the fluorescent HSA-recognizing nanoparticles [HSA]MIP-NGs of Example 1 are injected into the liver of a mouse.
Figure 8:
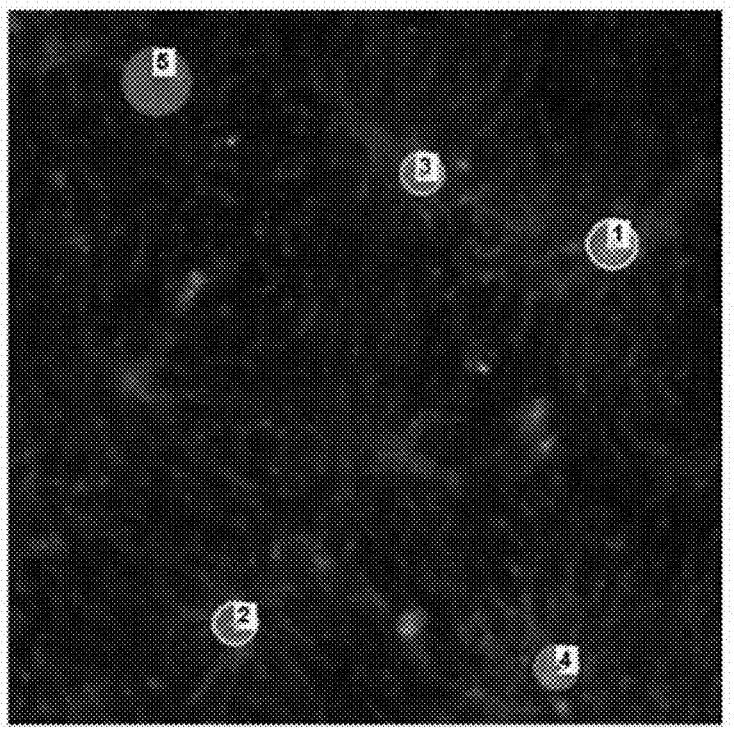

7-2. Experimental Results for Fluorescent HSA-Recognizing Nanoparticles [HSA]MIP-NGs FIG. 8(a) shows a confocal laser micrograph of the liver of the mouse at 10 minutes after the injection with the fluorescent HSA-recognizing nanoparticles [HSA]MIP-NGs of Example 1, and FIG. 8(b) shows a confocal laser micrograph of the liver of the mouse at 14 hours after the injection with the [HSA]MIP-NGs.

As shown in FIG. 8(a), the fluorescence derived from [HSA]MIP-NGs was clearly observed in the blood vessels of the liver immediately after the injection (after 10 minutes), and flowing of the [HSA]MIP-NGs through the blood vessels could be observed. On the other hand, as shown in FIG. 8(b), although the fluorescence intensity in the blood vessels was weakened at 14 hours after the injection, the fluorescence of the blood vessels could be clearly observed. Furthermore, since accumulation of the [HSA]MIP-NGs in hepatocytes was not observed, it became clear that the [HSA]MIP-NGs were not captured by hepatocytes and were nanoparticles excellent in retention in the blood.

Figure 9:
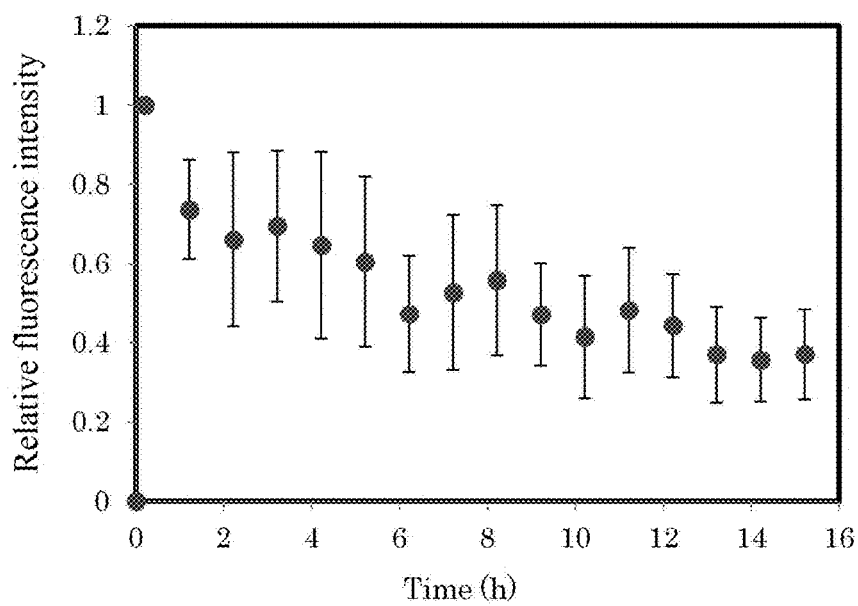
FIG. 9 shows the time course of fluorescence intensities in blood vessels in the liver of a mouse injected with the fluorescent HSA-recognizing nanoparticles [HSA]MIP-NGs of Example 1.

In order to investigate the retention of [HSA]MIP-NGs in the blood vessels, the time course of the fluorescence intensities at five points surrounded by circles in FIGS. 8(a) and 8(b) was obtained. The results are shown in FIG. 9. In FIG. 9, the horizontal axis indicates an elapsed time and the vertical axis indicates a relative fluorescence intensity. When the half-life was estimated from this FIG. 9, a high retention in the blood of approximately five and a half hours or more was shown.

7-3. Experimental Results on Fluorescent Reference Nanoparticles NIP-NGs

FIG. 10(a) shows a confocal laser micrograph of the mouse liver at 10 minutes after the injection with the fluorescent reference nanoparticles NIP-NGs of Comparative Example 1, and FIG. 10(b) shows a confocal laser micrograph of the mouse liver at 15 hours after the injection with the NIP-NGs.

As shown in FIG. 10(a), immediately after the injection (10 minutes later) of the fluorescent reference nanoparticles NIP-NGs, the blood vessels are clearly seen, whereas as shown in FIG. 10(b), when 15 hours elapsed after the injection of the fluorescent reference nanoparticles, the blood vessels are hardly seen and instead, it was observed that the NIP-NGs were taken up more frequently in the cells. These cells are considered to be hepatocytes. Furthermore, the number of hepatocytes emitting fluorescence was observed to increase with time.

Figure 10:
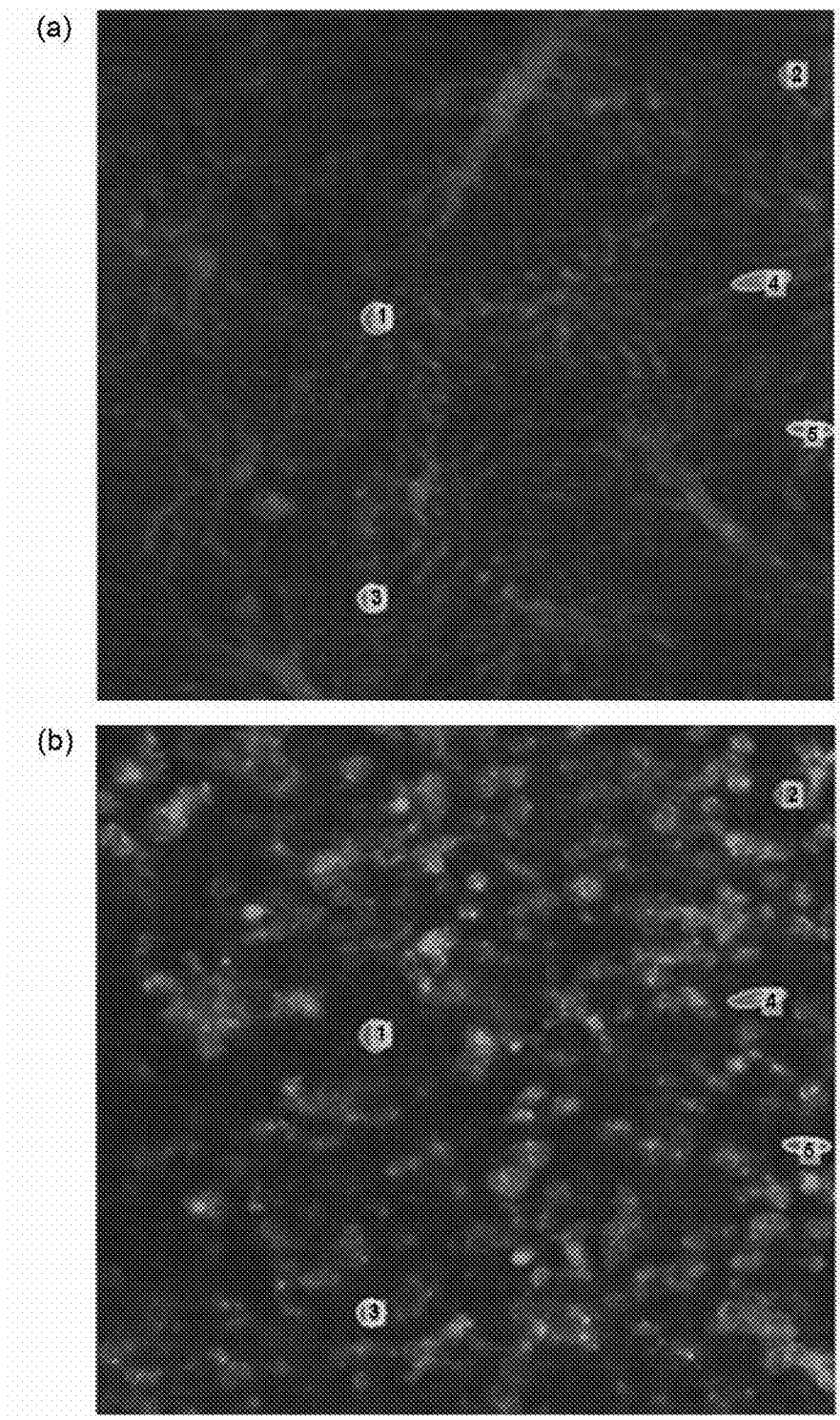
FIG. 10 shows confocal laser microscope photographs taken 10 minutes (a) and 15 hours (b) after the fluorescent reference nanoparticles NIP-NGs of Comparative Example 1 is injected into the liver of a mouse, together with the measurement points of blood vessels in the liver.
Figure 11:
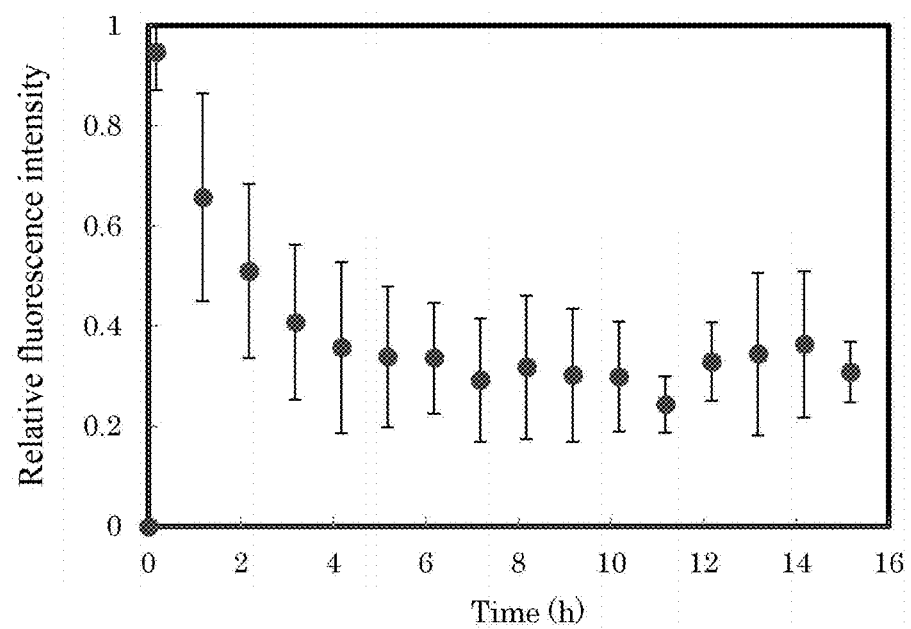
FIG. 11 shows the time course of fluorescence intensities in blood vessels in the liver of a mouse injected with the fluorescent reference nanoparticles NIP-NGs of Comparative Example 1.

In order to investigate the retention of the NIP-NGs in blood vessels, five places where the hepatocytes of FIG. 10(b) do not appear and in which blood vessels were initially visible were selected (shown as measurement points 1 to 5 in FIG. 10), and the time course of the fluorescence intensity in the place, that is, in the blood vessel, was measured. The results are shown in FIG. 11. As shown in FIG. 11, the tendency of disappearance from the blood vessel was observed in the NIP-NGs faster than in the [HSA]MIP-NGs (see FIG. 9), and the half-life thereof was measured to be 2 to 3 hours at 4 out of 5 places (measurement points 2 to 5). This data also revealed that retention of the [HSA]MIP-NGs in the blood was longer than that of the NIP-NGs.

Figure 12:
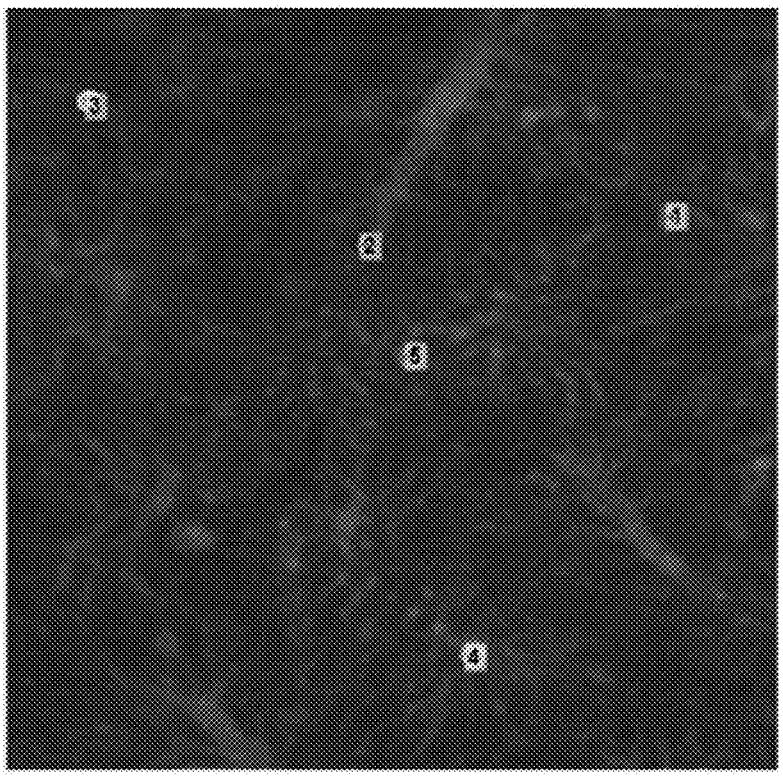
FIG. 12 shows the measurement points of hepatocytes in the photograph of FIG. 10, taken 10 minutes (a) and 15 hours (b) after the fluorescent reference nanoparticles NIP-NGs of Comparative Example 1 were injected into the liver of a mouse.
Figure 12:
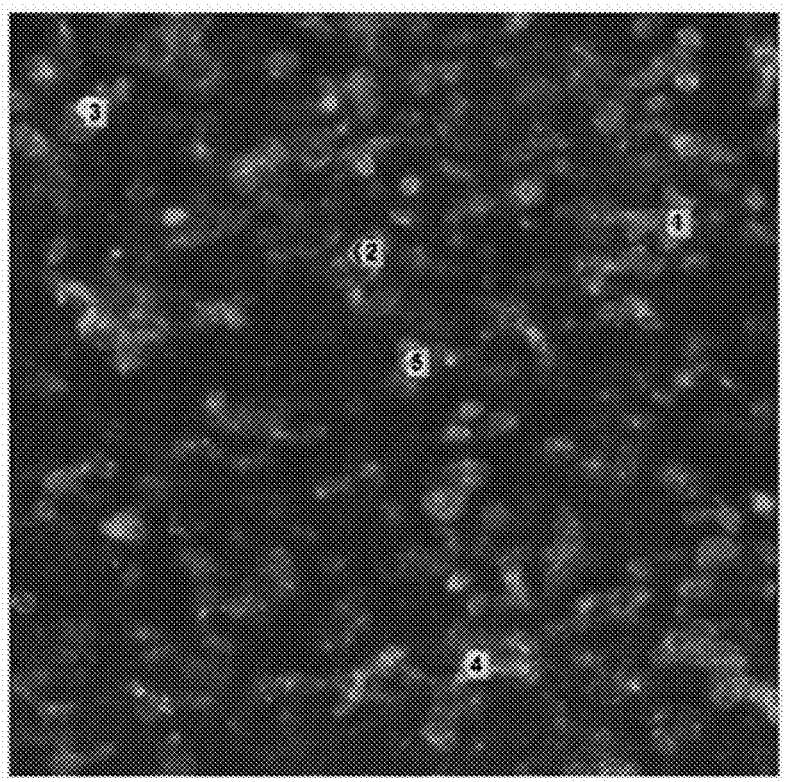

Next, the time course of the fluorescence intensity in the liver cells of the liver part of the mouse injected with the NIP-NGs was measured. In this measurement, five points (shown as measurement points 1 to 5 in FIG. 12) at which hepatocytes are visible with time in a confocal laser microscope image were measured for the fluorescence intensity. The measurement result is shown in FIG. 13.

Figure 13:
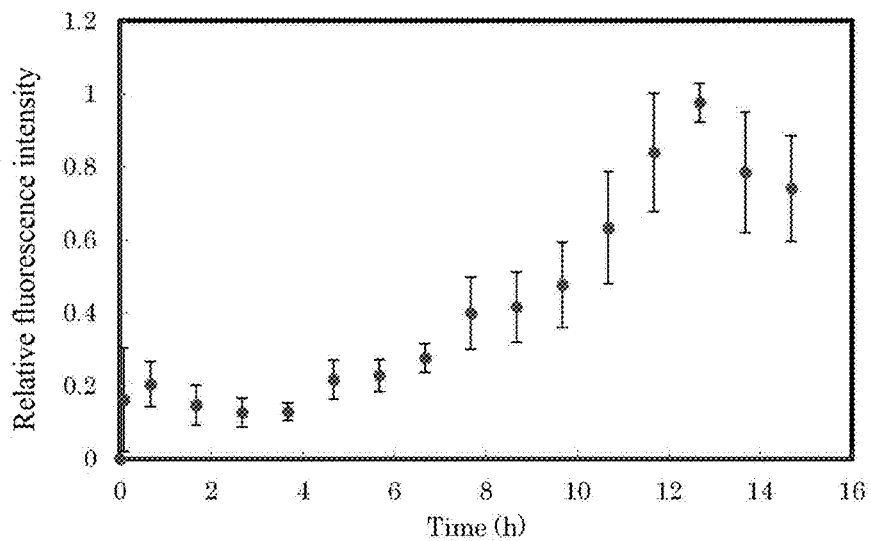
FIG. 13 shows the time course of fluorescence intensities of hepatocytes in the liver of a mouse injected with the fluorescent reference nanoparticles NIP-NGs of Comparative Example 1.

As shown in FIG. 13, it was observed that fluorescence intensities in hepatocytes increased over time at all the measurement points with time. This is a result clearly suggesting uptake of nanoparticles into hepatocytes, and it was revealed again that the NIP-NGs were taken into the hepatocytes, that is, the retention of the NIP-NGs in the blood was low. On the other hand, the [HSA]MIP-NGs was not taken up into hepatocytes (see FIG. 8), so it is considered that high stealth property could be obtained in the blood as was expected.

8. Example 2: Synthesis of Drug-Loaded HSA-Recognizing Nanoparticles DOX1-[HSA]MIP-NGs

8-1. Synthesis of Doxorubicin Methacrylate (DOXMA-1) Having Amide Bond

[Chem. 2]

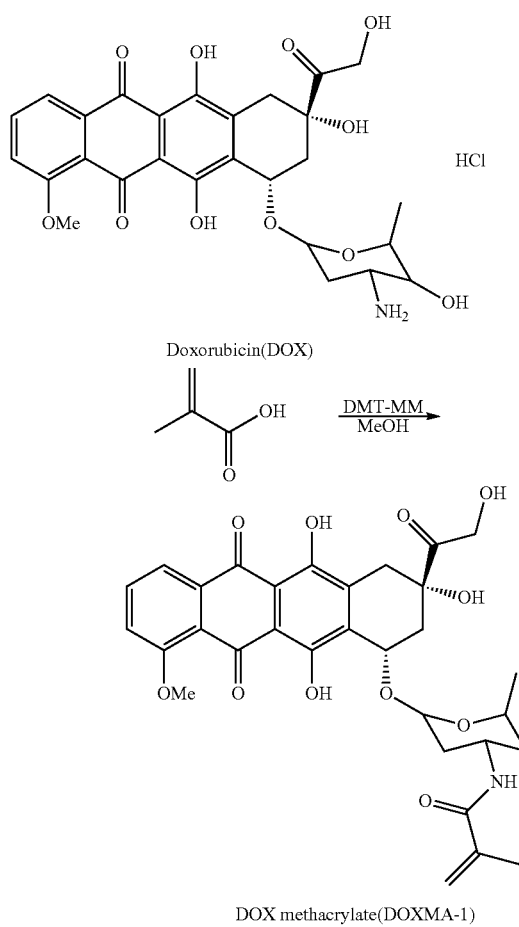

Anticancer drug doxorubicin HCl (58 mg, 0.10 mmol) was dissolved in 30 mL of MeOH containing 30 μL (0.40 mmol) of Et$_3$N, and 10 mL of MeOH in which 8.5 μL (0.10 mmol) of methacrylic acid and 27.7 mg (0.10 mmol) of DMT-MM were dissolved was added using a dropping funnel. After allowing the mixture to stand overnight, a spot of the raw material and a spot considered to be the object were observed at an Rf value of 0.25 and an Rf value of 0.75, respectively, by TLC (1-BuOH:AcOH:H$_2$O=4:1:5). Since many raw material spots remained, 10 mL of MeOH in which 19 μL (0.20 mmol) of methacrylic acid and 27.7 mg (0.10 mmol) of DMT-MM were dissolved was further added and reacted. After solvent substitution with EtOAc, the reaction solution was washed three times with sodium bicarbonate water. After dehydration with MgSO$_4$, the reaction solution was subjected to distillation under reduced pressure and then vacuum drying, and the desired product was identified by $^1$H-NMR.

Confirmation of synthesis of DOX methacrylate (DOXMA-1) which is the objective substance was performed by $^1$H-NMR. Specifically, a new appearance of a peak derived from the methacryloyl group of the product was confirmed.

$^1$H-NMR chart. 1 (300 MHz, DMSO-d$_6$)
δ=14.04 (br, 1H), δ=13.28 (br, 1H), δ=7.94, 7.67, 7.33 (m, 3H), δ=5.60, 5.47 (m, 2H), δ=5.27 (d, 2H), δ=4.95 (br, 1H), δ=4.83 (m, 2H), δ=4.56 (m, 2H), δ=4.16 (m, 1H), δ=3.97 (s, 3H), δ=3.43 (s, 1H), δ=2.97 (br, 2H), δ=2.18 (m, 1H), δ=1.97 (m, 1H), δ=1.78 (s, 3H), δ=1.47 (m, 1H), δ=1.17 (d, 3H)

8-2. Synthesis of Drug-Loaded HSA-Recognizing Nanoparticles DOX1-[HSA]MIP-NGs The obtained DOXMA-1 was copolymerized in an emulsifier-free precipitation polymerization system to synthesize [HSA]MIP-NGs having an HSA recognition space (DOX1-[HSA]MIP-NGs) while carrying a drug. Specific components and compositions for constructing the copolymerization reaction system are shown in Table 2 below. The polymerization was carried out by the reaction in a Schlenk flask under a nitrogen atmosphere at 70° C. for 12 hours.

TABLE 2

| | | |
|---|---|---|
| NIPAm | Water-soluble monomer | 203.5 mg (1.8 mmol) |
| MBAA | Crosslinking agent | 15.4 mg (0.10 mmol) |
| MPC | Biocompatible monomer | 29.5 mg (0.10 mmol) |
| PyA | Functional monomer | 21.0 mg (0.10 mmol) |
| DOXMA-1 | Drug monomer | 6.1 mg (0.009 mmol) |
| FAm | Fluorescent monomer | 2.0 mg (0.005 mmol) |
| HSA | Target protein | 6.6 mg (0.10 μmol) |
| V-50 | Initiator | 108 mg (0.40 mmol) |
| 10 mM PBS (pH 7.4) | Solvent | 50 mL |

Figure 14:
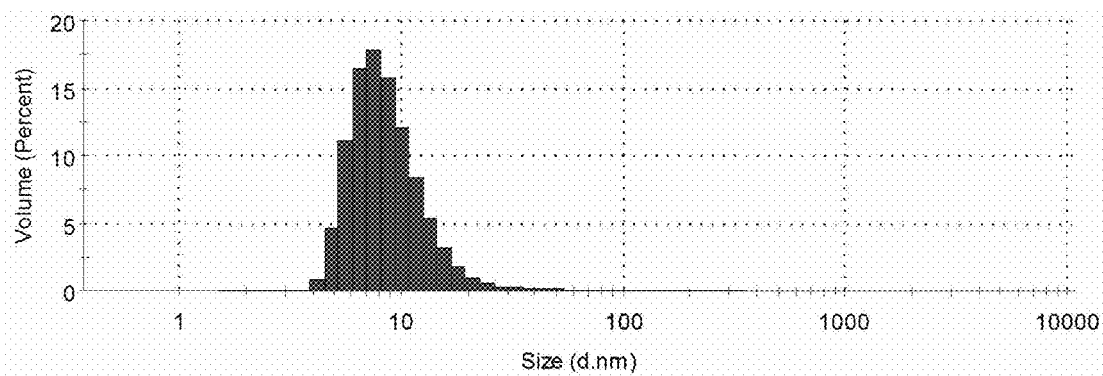
FIG. 14 shows the particle size distribution obtained by DLS of the drug-loaded HSA-recognizing nanoparticles DOX1-[HSA]MIP-NGs of Example 2.

9. Purification and Average Particle Diameter Measurement of Drug-Loaded HSA-Recognizing Nanoparticles DOX1-[HSA]MIP-NGs The emulsion obtained by polymerization was subjected to a size exclusion chromatography using Sephadex G-100 to purify the drug-loaded HSA-recognizing nanoparticles DOX1-[HSA]MIP-NGs. Thereafter, the particle diameter of the drug-loaded HSA-recognizing nanoparticles DOX1-[HSA]MIP-NGs was measured by a dynamic light scattering method. As a result of the DLS measurement, the Z-average particle diameter was 37 nm (PDI: 0.49). FIG. 14 shows the particle size distribution of the drug-loaded HSA-recognizing nanoparticles DOX1-[HSA]MIP-NGs obtained by the DLS. From this, it is considered that nano-sized MIP particles could be obtained even in the drug-loaded type [HSA]MIP-NGs like the drug-unloaded type [HSA]MIP-NGs of Example 1.

10. HSA Binding Experiment of DOX1-[HSA]MIP-NGs by Surface Plasmon Resonance Method (SPR)

An HSA-immobilized gold substrate was prepared in the same manner as in item 5-1 of Example 1, and the adsorption behavior of the drug-loaded HSA-recognizing nanoparticles DOX1-[HSA]MIP-NGs was confirmed using the obtained HSA-immobilized gold substrate, in the same manner as in item 5-2.

Figure 15:
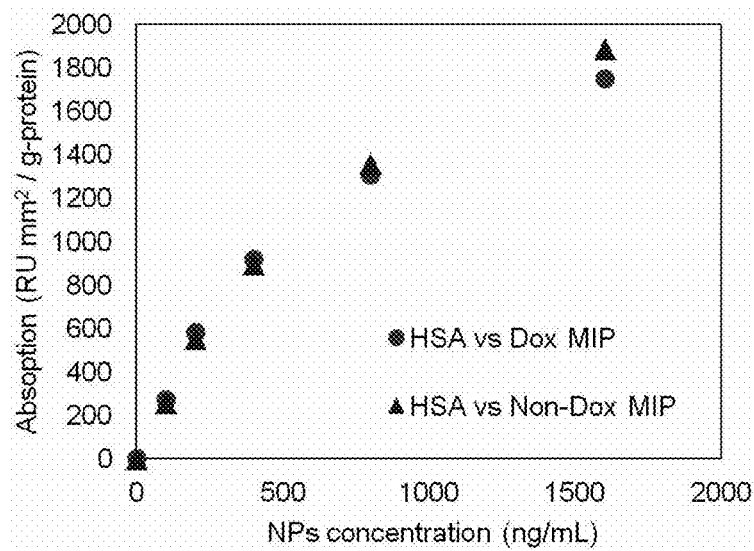
FIG. 15 is a graph showing the adsorption behavior (HSA vs Dox MIP) of the drug-loaded HSA-recognizing nanoparticles DOX1-[HSA]MIP-NGs of Example 2 to the HSA-immobilized gold substrate, together with the adsorption behavior (HSA vs Non-Dox MIP) of the drug-unloaded HSA-recognizing nanoparticles [HSA]MIP-NGs of Example 1.

The relationship (n=2) between the adsorption amount (absorption (RU mm$^2$/g-protein) and particle concentration (NPs concentration (ng/nL) of the drug-loaded HSA-recognizing nanoparticles DOX1[HSA]MIP-NGs in the adsorption behavior on the HSA-immobilized gold substrate is shown in FIG. 15. The adsorption amount for HSA is defined by the amount of HSA immobilized on the SPR sensor chip. In FIG. 15, the adsorption behavior (HSA vs Non-Dox MIP) of the drug-unloaded HSA-recognizing nanoparticles [HSA]MIP-NGs of Example 1 is also shown together with the adsorption behavior (HSA vs Dox MIP) of the drug-loaded HSA-recognizing nanoparticles DOX1-[HSA]MIP-NGs.

As shown in FIG. 15, it was confirmed that the behavior of the drug-loaded HSA-recognizing nanoparticles DOX1-[HSA]MIP-NGs of this Example is shown to be similar to that of the drug-unloaded HSA-recognizing nanoparticles [HSA]MIP-NGs of Example 1. Therefore, it was suggested that the drug-loaded HSA-recognizing nanoparticle DOX1-[HSA]MIP-NGs have the same HSA binding space as the drug-unloaded HSA-recognizing nanoparticles [HSA]MIP-NGs of Example 1.

11. Observation of Uptake of Drug-Unloaded HSA-Recognizing Nanoparticles [HSA]MIP-NGs and Drug-Loaded HSA-Recognizing Nanoparticles DOX1-[HSA]MIP-NGs into Cells Uptake of the nanoparticles of the present invention into cells was observed and the usefulness in DDS was confirmed.

11-1. Uptake into Fibroblast NIH/3T3

Fibroblast cells NIH/3T3 were seeded on a glass dish for confocal observation using serum D-MEM medium so that the number of cells was 240,000 cells/dish, and the cells were left standing in a $CO_2$ incubator for 24 hours. Thereafter, 200 μL of the purified drug-unloaded HSA-recognizing nanoparticle [HSA]MIP-NGs of Example 1 was added to have a concentration of 100 μg/mL, and the mixture was allowed to stand still for further 24 hours in a $CO_2$ incubator. The sample was washed with a serum D-MEM medium before observation.

The cells were observed using a confocal laser microscope. The observation conditions are as follows.

Confocal laser microscope: IX 81 manufactured by Olympus Corporation.

Objective lens: 100×(oil)

Filter used: FITC

Figure 16:
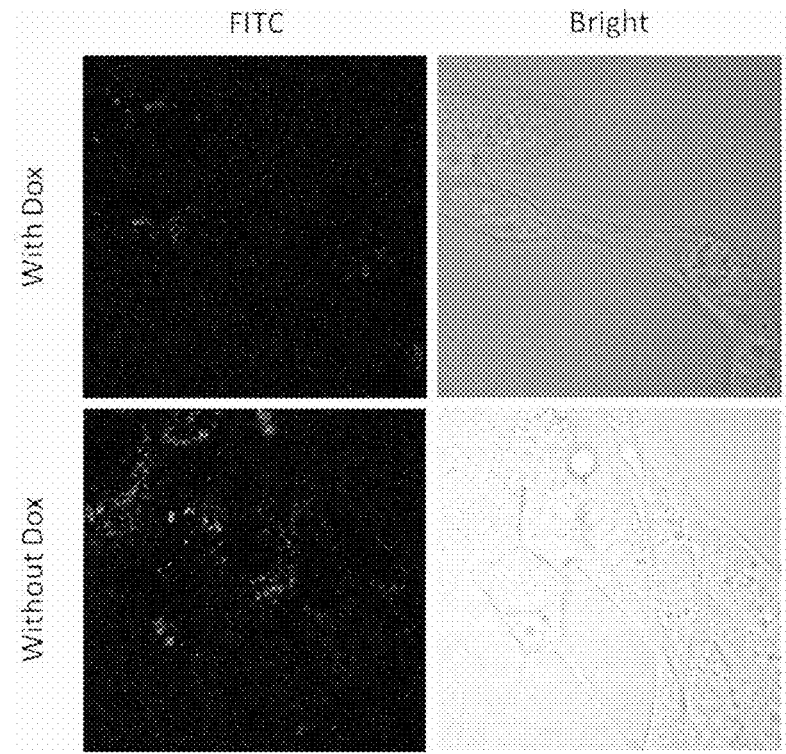
FIG. 16 shows the results of observation of uptake into fibroblast NIH/3T3 on the drug-unloaded HSA-recognizing nanoparticles [HSA]MIP-NGs of Example 1 (Without Dox) and the drug-loaded HSA-recognizing nanoparticles DOX1-[HSA]MIP-NGs of Example 2 (With Dox).

The observation result is shown in "Without Dox" of FIG. 16. In FIG. 16, "FITC" is a fluorescent image of nanoparticles and "Bright" is a bright field image.

As shown in "Without Dox" in FIG. 16, fluorescence derived from the drug-unloaded HSA-recognizing nanoparticles [HSA]MIP-NGs was observed clearly in the cells. That is, it was revealed that the drug-unloaded HSA-recognizing nanoparticles [HSA]MIP-NGs are incorporated into the cells.

Similar experiments and observations were also performed on the drug-loaded HSA-recognizing nanoparticles DOX1-[HSA]MIP-NGs. The observation result is shown in "With Dox" in FIG. 16.

As shown in "With Dox" in FIG. 16, it was revealed that the drug-loaded HSA-recognizing nanoparticles DOX1-[HSA]MIP-NGs were also incorporated into the cells.

11-2. Uptake into Human Breast Cancer Cells (Hela Cells)

As for the human breast cancer cells, i.e. Hela cells, uptake of the drug-unloaded HSA-recognizing nanoparticles [HSA]MIP-NGs and the drug-loaded HSA-recognizing nanoparticles DOX1-[HSA]MIP-NGs was observed in the same manner as in the above item 11-1.

Figure 17:
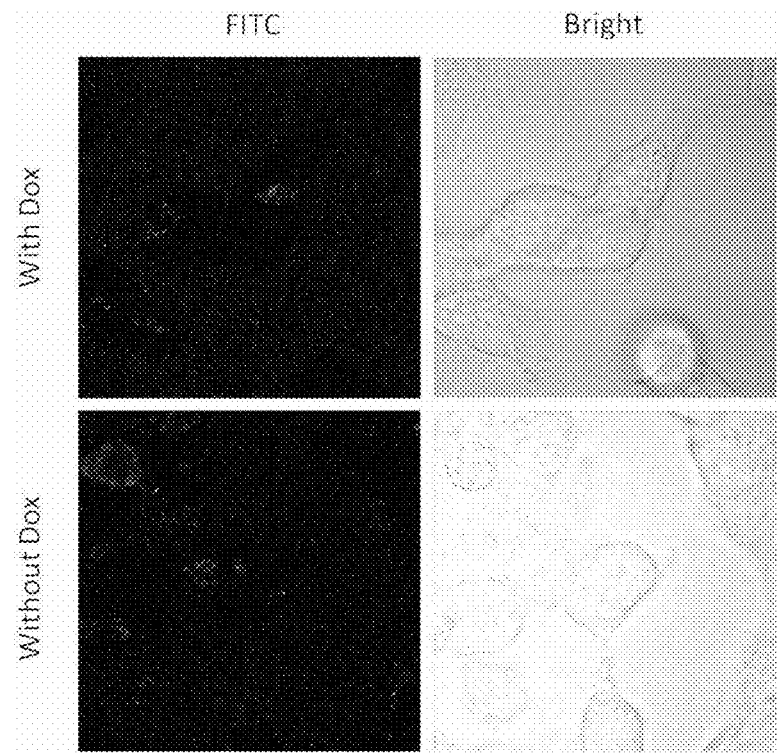
FIG. 17 shows the results of observation of uptake into human breast cancer cells, i.e. Hela cells, on the drug-unloaded HSA-recognizing nanoparticles [HSA]MIP-NGs of Example 1 (Without Dox) and the drug-loaded HSA-recognizing nanoparticles DOX1-[HSA]MIP-NGs of Example 2 (With Dox).

The observation results are shown in "Without Dox" ([HSA]MIP-NGs) and "With Dox" (DOX-[HSA]MIP-NGs) in FIG. 17. As shown in FIG. 17, it became clear that the drug-unloaded HSA-recognizing nanoparticles [HSA]MIP-NGs and the drug-loaded HSA-recognizing nanoparticles DOX1-[HSA]MIP-NGs are incorporated into human breast cancer cells. i.e. Hela cells.

12. Example 3: Synthesis of Another Protein-Recognizing Nanoparticles [MSA]MIP-NGs Fluorescent MSA-recognizing nanoparticles [MSA]MIP-NGs were synthesized in the same manner as in the item 1-1 (Example 1), except that the target protein was changed to mouse serum albumin (MSA) instead of human serum albumin (HSA). Specific components and compositions for constructing the copolymerization reaction system are shown in Table 3 below.

TABLE 3

| NIPAm | Water-soluble monomer | 407 mg (3.6 mmol) |
|---|---|---|
| MBAA | Crosslinking agent | 30.8 mg (0.20 mmol) |
| MPC | Biocompatible monomer | 59.0 mg (0.20 mmol) |
| PyA | Functional monomer | 42.0 mg (0.20 mmol) |
| FAm | Fluorescent monomer | 4.0 mg (0.01 mmol) |
| MSA | Target protein | 13.2 mg (0.20 μmol) |
| V-50 | Initiator | 216 mg (0.80 mmol) |
| PBS | Solvent | 100 mL |

The obtained fluorescent MSA-recognizing nanoparticles [MSA]MIP-NGs were purified in the same manner as in the above item 2, except that Sephadex G-100 was used in place of Sephadex G-50, and the particle diameter was determined by the DLS measurement.

Figure 18:
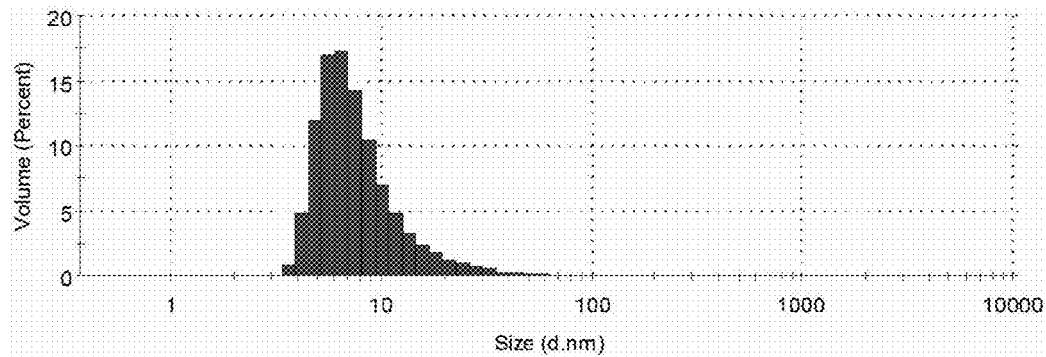
FIG. 18 shows the particle size distribution obtained by DLS of the fluorescent MSA-recognizing nanoparticles [MSA]MIP-NGs of Example 3.

FIG. 18 shows the particle size distribution of the fluorescent MSA-recognizing nanoparticles [MSA]MIP-NGs obtained by the DLS. From this, it is considered that also in this Example, nano-sized MIP particles could be similarly obtained like the [HSA]MIP-NGs of Example 1 and the drug-loaded [HSA]MIP-NGs of Example 2.

13. Bonding Characteristics of [MSA]MIP-NGs by Surface Plasmon Resonance Method (SPR)

An HSA-immobilized gold substrate was prepared in the same manner as the item 5-1 in Example 1; an MSA-immobilized gold substrate was prepared in the same manner, except that MSA (mouse blood albumin) was used in place of HSA; and an IgG-immobilized gold substrate was prepared in the same manner, except that IgG was used in place of HSA.

The adsorption behavior of the fluorescent MSA-recognizing nanoparticles [MSA]MIP-NGs was confirmed for each of various protein-immobilized gold substrates in the same manner as in the item 5-2.

Figure 19:
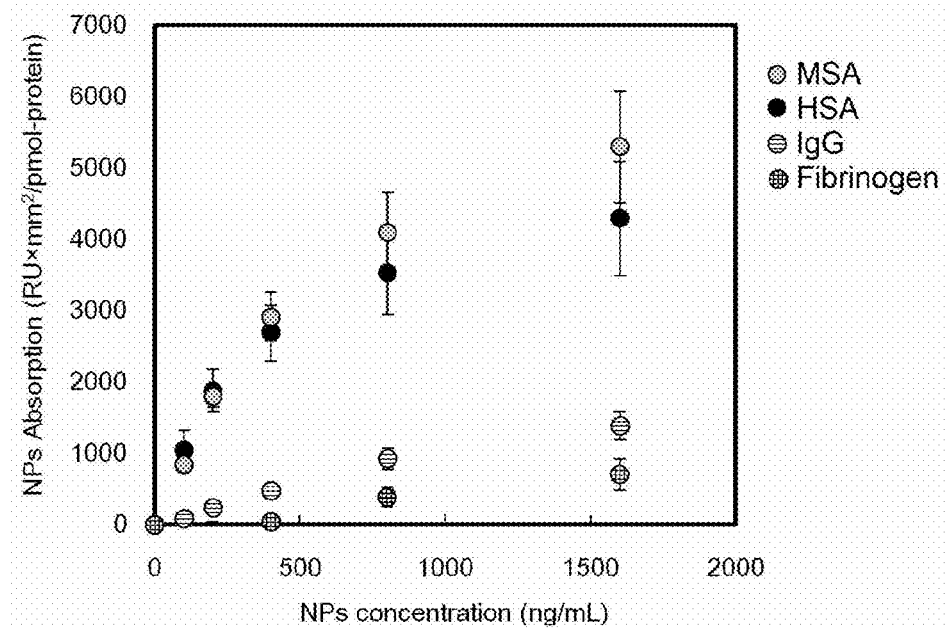
FIG. 19 shows the adsorption behavior of the fluorescent MSA-recognizing nanoparticles [MSA]MIP-NGs of Example 3 on various proteins-immobilized gold substrates.

With respect to the adsorption behavior of the fluorescent MSA-recognizing nanoparticles [MSA]MIP-NGs on each protein-immobilized gold substrate, the relationship between adsorption amount of the nanoparticles (NPs Absorption (RU×$mm^2$/pmol-protein) and particle concentration (NPs concentration (ng/mL)) is shown in FIG. 19. As shown in FIG. 19, the fluorescent MSA-recognizing nanoparticles [MSA]MIP-NGs has a low binding capacity for IgG and fibrinogen like the fluorescent HSA-recognizing nanoparticles [HSA]MIP-NGs of Example 1. On the other hand, the binding amount to MSA in the high concentration region is higher than the binding amount to HSA, suggesting that a recognition space for MSA is formed. Therefore, it was shown that the nanoparticles of the present invention can be obtained also for proteins other than HSA.

14. Example 4: Synthesis of Non-Fluorescent Drug-Loaded HSA-Recognizing Nanoparticles NF-DOX1-[HSA]MIP-NGs The non-fluorescent drug-loaded HSA-recognizing nanoparticles NF-DOX-[HSA]MIP-NGs were synthesized by performing copolymerization basically in an emulsifier-free precipitation polymerization system in the same manner as in Example 2, except that the fluorescent monomer FAm was not used. Specific components and compositions for constructing the copolymerization reaction system are shown in Table 4 below. The polymerization was carried out by the reaction in a Schlenk flask under a nitrogen atmosphere at 70° C. for 12 hours.

TABLE 4

| NIPAm | Water-soluble monomer | 203.5 mg (1.8 mmol) |
| --- | --- | --- |
| MBAA | Crosslinking agent | 15.4 mg (0.10 mmol) |
| MPC | Biocompatible monomer | 29.5 mg (0.10 mmol) |
| PyA | Functional monomer | 21.0 mg (0.10 mmol) |
| DOXMA-1 | Drug monomer | 12 mg (0.02 mmol) |
| HSA | Target protein | 6.6 mg (0.10 μmol) |

TABLE 4-continued

| V-50 | Initiator | 108 mg (0.40 mmol) |
| --- | --- | --- |
| 10 mM PBS (pH 7.4) | Solvent | 50 mL |

Figure 20:
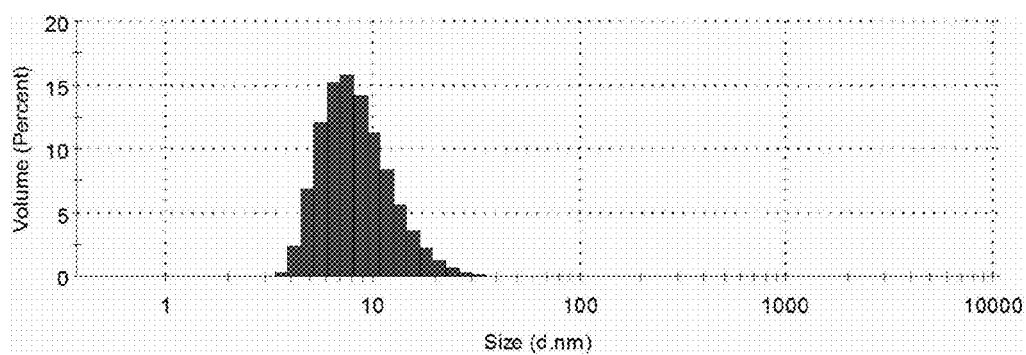
FIG. 20 shows the particle size distribution obtained by DLS of the non-fluorescent drug-loaded HSA-recognizing nanoparticle NF-DOX1-[HSA]MIP-NGs of Example 4.
Figure 21:
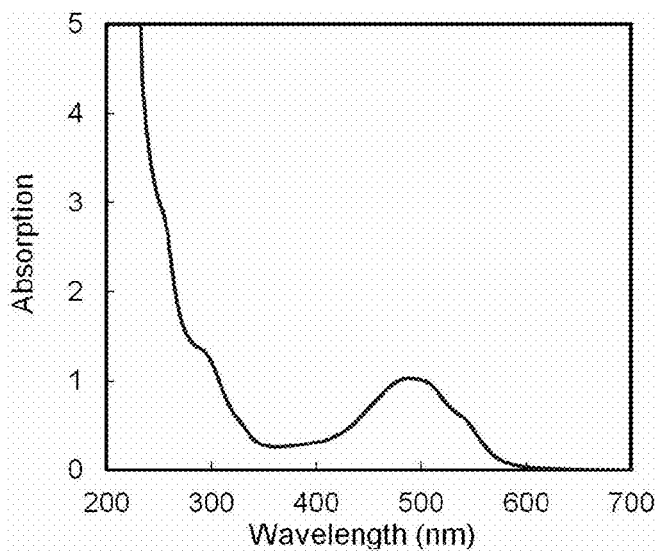
FIG. 21 shows the UV-vis spectrum of the non-fluorescent drug-loaded HSA-recognizing nanoparticles NF-DOX1-[HSA]MIP-NGs of Example 4.

15. Purification and Average Particle Diameter Measurement of Non-Fluorescent Drug-Loaded HSA-Recognizing Nanoparticles NF-DOX1-[HSA]MIP-NGs The emulsion obtained by the polymerization was subjected to a size exclusion chromatography using Sephadex G-100 to purify the non-fluorescent drug-loaded HSA-recognizing nanoparticles NF-DOX1-[HSA]MIP-NGs. Thereafter, the particle diameter of the non-fluorescent drug-loaded HSA-recognizing nanoparticles NF-DOX1-[HSA]MIP-NGs was measured by a dynamic light scattering method. As a result of the DLS measurement, the Z-average particle diameter was 17 nm (PDI: 0.46). FIG. 20 shows the particle size distribution of the non-fluorescent drug-loaded HSA-recognizing nanoparticles NF-DOX1-[HSA]MIP-NGs obtained by the DLS. Also, FIG. 21 shows the UV-Vis spectrum of the non-fluorescent drug-loaded HSA-recognizing nanoparticles NF-DOX1-[HSA]MIP-NGs. From these results, it was suggested that an absorption region derived from doxorubicin was present and the anticancer agent was enclosed in the particles.

16. Example 5: Synthesis of Non-Fluorescent Drug-Loaded HSA-Recognizing Nanoparticles NF-DOX2-[HSA]MIP-NGs

16-1. Synthesis of Doxorubicin Methacrylate (DOXMA-2) Having Hydrazone Bond

[Chem. 3]

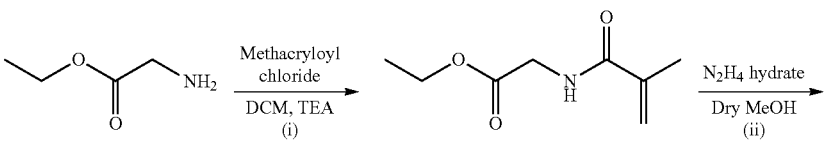

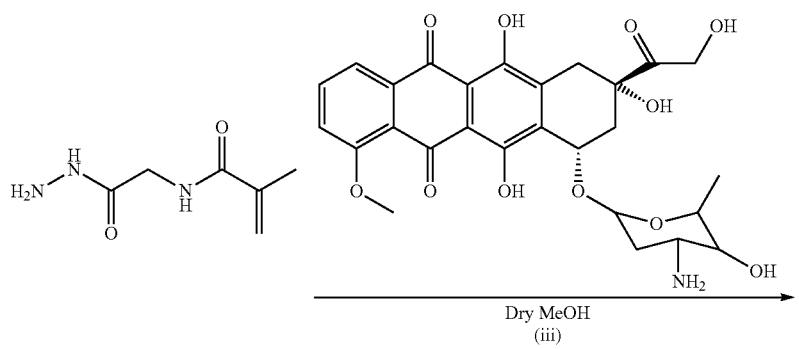

-continued

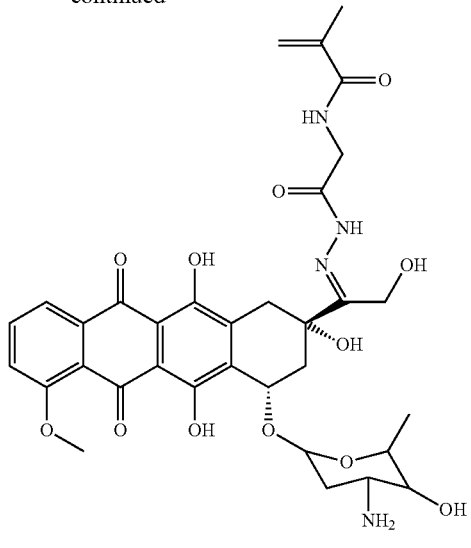

DOXMA-2

(i) Synthesis of Ethyl Glycinate Methacrylate

After dissolving ethyl glycinate hydrochloride (5.0 g, 36 mmol) and triethylamine (10 mL, 72 mmol) in DCM (50 mL), a solution of methacryloyl chloride (3.78 g, 36 mmol) dissolved in DCM (30 mL) was added dropwise thereto in a nitrogen atmosphere under ice-cooling. The mixture was reacted overnight at room temperature and then washed three times with each of brine, aqueous solution of citric acid and aqueous solution of sodium carbonate, and once with brine again. After washing, purification was carried out by silica gel column chromatography (hexane:ethyl acetate=100:00 to 50:50). After drying under reduced pressure, vacuum drying was carried out to identify the target substance by $^1$H-NMR.

The synthesis of ethyl glycinate methacrylate as the target substance was confirmed by $^1$H-NMR.

$^1$H-NMR (300 MHz, DMSO-$d_6$):

δ=8.35 (br, 1H), δ=5.71 (s, 1H), 5.39 (s, 1H), δ=4.07 (q, 2H), δ=3.82 (m, 2H), δ=1.85 (s, 3H), δ=1.09 (t, 3H)

(ii) Synthesis of Methacryloyl Glycine Hydrazide

Ethyl glycinate methacrylate (0.5 g, 3.0 mmol) and hydrazine hydrate (200 mg, 6.0 mmol) were mixed in anhydrous methanol (10 mL) and reacted overnight at room temperature. Thereafter, the solvent was removed under reduced pressure and the residue was purified by silica gel chromatography (EtOAc:MeOH=100:00 to 500:50). After drying under reduced pressure, vacuum drying was carried out and the desired product was identified by $^1$H-NMR.

Confirmation of the synthesis of methacryloyl glycine hydrazide as the target substance was performed by $^1$H-NMR $^1$H-NMR (300 MHz. DMSO-$d_6$):

δ=9.00 (br, 1H), δ=8.10 (br, 1H), δ=5.72 (s, 1H), δ=5.33 (s, 1H), δ=4.16 (b, 2H), δ=3.65 (m, 2H), δ=1.87 (s, 3H)

(iii) Synthesis of Methacryloyl Glycine Hydrazone-DOX (DOXMA-2)

Methacryloyl glycine hydrazide (14.5 mg, 0.1 mmol) and DOX hydrochloride (29 mg, 0.05 mmol) were mixed in anhydrous methanol (10 mL) and reacted overnight at room temperature. After that, the solvent was removed under reduced pressure, and the progress of the reaction was confirmed by MALDI-TOF-MS.

The reaction progress of the objective methacryloyl glycine hydrazone-DOX (DOXMA-2) was confirmed by MALDI-TOF-MS.

MALDI-TOF-MS (matrix: CHCA): m/z=724.04 [M+Na].

16-2. Synthesis of Non-Fluorescent Drug-Loaded HSA-Recognizing Nanoparticles NF-DOX2-[HSA]MIP-NGs Copolymerization was carried out in an emulsifier-free precipitation polymerization system basically in the same manner as in Example, except that the DOXMA-2 obtained above was used as the drug monomer and no fluorescent monomer FAm was added, thereby to synthesize non-fluorescent drug-loaded HSA-recognizing nanoparticles NF-DOX2-[HSA]MIP-NGs. Specific components and compositions for constructing the copolymerization reaction system are shown in Table 5 below. The polymerization was carried out by the reaction in a Schlenk flask under a nitrogen atmosphere at 70° C. for 12 hours.

TABLE 5

| NIPAm | Water-soluble monomer | 203.5 mg (1.8 mmol) |
|---|---|---|
| MBAA | Crosslinking agent | 15.4 mg (0.10 mmol) |
| MPC | Biocompatible monomer | 29.5 mg (0.10 mmol) |
| PyA | Functional monomer | 21.0 mg (0.10 mmol) |
| DOXMA-2 | Drug monomer | 15 mg (0.02 mmol) |
| HSA | Target protein | 6.6 mg (0.10 μmol) |
| V-50 | Initiator | 108 mg (0.40 mmol) |
| 10 mM PBS (pH 7.4) | Solvent | 50 mL |

Figure 22:
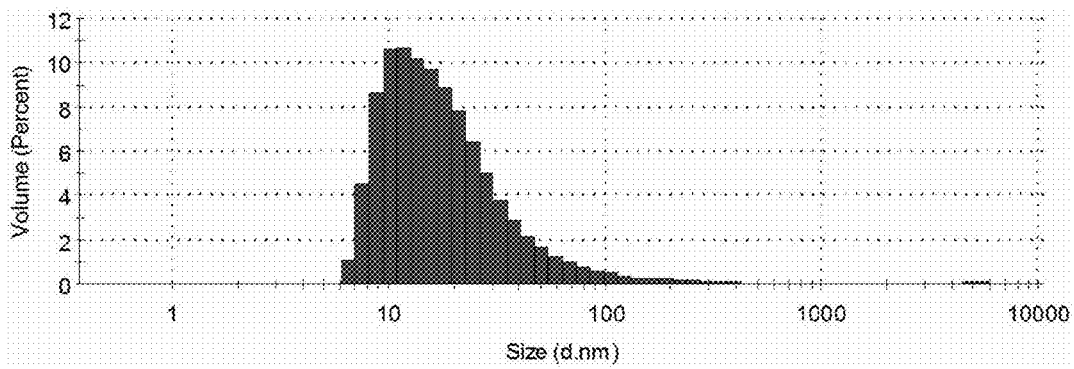
FIG. 22 shows the particle size distribution obtained by DLS of the non-fluorescent drug-loaded HSA-recognizing nanoparticles NF-DOX2-[HSA]MIP-NGs of Example 5.
Figure 23:
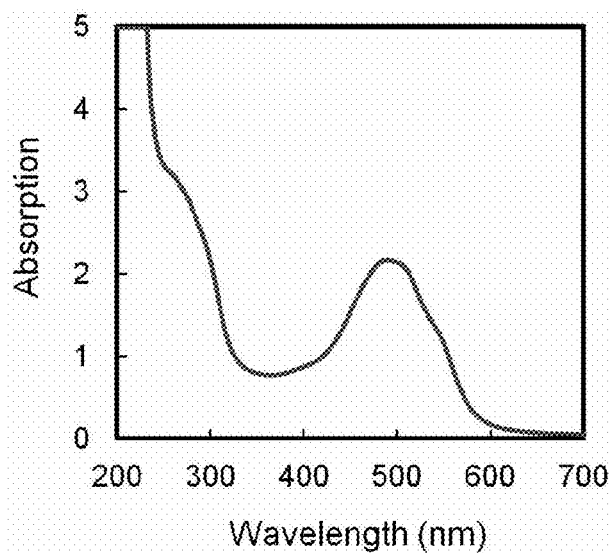
FIG. 23 shows the UV-vis spectrum of the non-fluorescent drug-loaded HSA-recognizing nanoparticles NF-DOX2-[HSA]MIP-NGs of Example 5.

17. Purification and Average Particle Diameter Measurement of Non-Fluorescent Drug-Loaded HSA-Recognizing Nanoparticles NF-DOX2-[HSA]MIP-NGs The emulsion obtained by the polymerization was subjected to a size exclusion chromatography using Sephadex G-100 to purify non-fluorescent drug-loaded HSA-recognizing nanoparticles NF-DOX2-[HSA]MIP-NGs. Thereafter, the particle diameter of the non-fluorescent drug-loaded HSA-recognizing nanoparticles NF-DOX2-[HSA]MIP-NGs was measured by a dynamic light scattering method. As a result of the DLS measurement, the Z-average particle diameter was found to be 81 nm (PDI: 0.45). FIG. 22 shows the particle size distribution of the non-fluorescent drug-loaded HSA-recognizing nanoparticles NF-DOX2-[HSA] MIP-NGs obtained by the DLS. FIG. 23 shows the UV-Vis spectrum of the non-fluorescent drug-loaded HSA-recognizing nanoparticles NF-DOX2-[HSA]MIP-NGs. From these results, it was suggested that an absorption region derived from doxorubicin was present and the anticancer agent was enclosed in the particles.

18. MTT Test

18-1. Sample

Using a serum-free D-MEM medium in a 96-microwell plate, 100 μL of NIH/3T3 cells was seeded in each well at a density of 5000 cells/well and allowed to stand still in a $CO_2$ incubator for 24 hours. Thereafter, the non-fluorescent drug-loaded HSA-recognizing nanoparticles NF-DOX1-[HSA]MIP-NGs of Example 4 and the non-fluorescent drug-loaded HSA-recognizing nanoparticles NF-DOX2-[HSA] MIP-NGs of Example 5 were added in an amount of 10 μL each to a concentration of 0 to 100 μg/mL, and the mixture was allowed to stand still for further 24 hours in a $CO_2$ incubator.

Further, 10 μL of the MTT reagent dissolved in PBS buffer to a concentration of 5 mg/mL was added to each well, and a color reaction of 2 hours was carried out. Thereafter, 200 μL of PBS buffer was added and allowed to stand still for 1 minute. After removal of the solvent, 200 μL of 0.04 M HCl/isopropyl alcohol was added to each well, and formazan was dissolved by shaking for 10 minutes with a shaker. Absorbance was measured using this solution.

18-2. Blank-A

The absorbance was measured in the same manner as in the item 18-1, except that NIH/3T3 cells were not added.

18-3. Control

The absorbance was measured in the same manner as in the item 18-1 above, except that the non-fluorescent drug-loaded HSA-recognizing nanoparticles NF-DOX1-[HSA] MIP-NGs of Example 4 and the non-fluorescent drug-loaded HSA-recognizing nanoparticles NF-DOX2-[HSA]MIP-NGs of Example 5 were not added.

18-4. Blank-B

The absorbance was measured in the same manner as in the item 18-1, except that the NIH/3T3 cells as well as the non-fluorescent drug-loaded HSA-recognizing nanoparticles NF-DOX1-[HSA]MIP-NGs of Example 4 and the non-fluorescent drug-loaded HSA-recognizing nanoparticles NF-DOX2-[HSA]MIP-NGs of Example 5 were not added.

18-5. Cell Viability

The classification and breakdown of each sample for which the absorbance was measured are shown in Table 6 below.

TABLE 6

| | Cells | Particles | MTT | |
|---|---|---|---|---|
| sample | ○ | ○ | ○ | sample-blank-A |
| blank-A | x | ○ | ○ | =Absorbance of cells affected by particles |
| control | ○ | x | ○ | control-blank-B |
| blank-B | x | x | ○ | =Absorbance of cells not affected by particles |

From these absorbances, cell viability was calculated based on the following formula.

$$\text{Cell viability (\%)} = \frac{\text{sample }(A_{570} - A_{650}) - \text{blankA }(A_{570} - A_{650})}{\text{control }(A_{570} - A_{650}) - \text{blankB }(A_{570} - A_{650})} \times 100 \quad [\text{Math. 2}]$$

Figure 24:
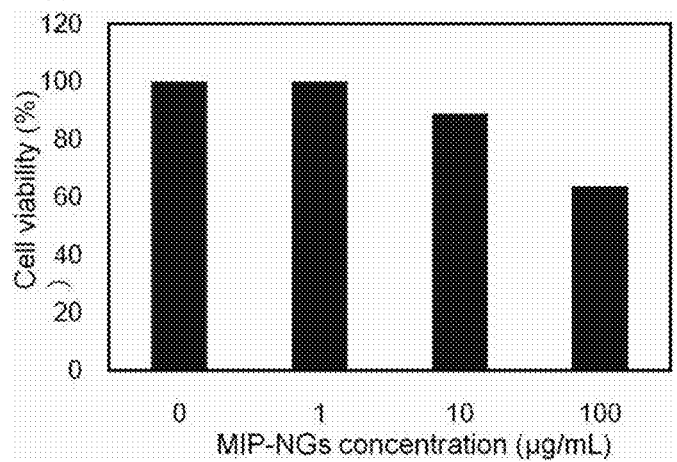
FIG. 24 shows the relationship between the concentration and the cell viability of the non-fluorescent drug-loaded HSA-recognizing nanoparticles NF-DOX1-[HSA]MIP-NGs of Example 4.
Figure 25:
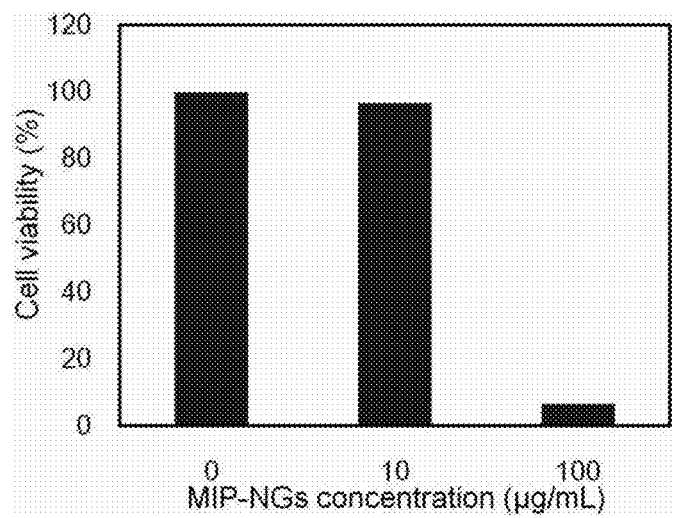
FIG. 25 shows the relationship between the concentration and the cell viability of the non-fluorescent drug-loaded HSA-recognizing nanoparticles NF-DOX2-[HSA]MIP-NGs of Example 5.

FIG. 24 shows the relationship between the concentration (MIP-NGs concentration (μg/mL)) and the cell viability (%) of the non-fluorescent drug-loaded HSA-recognizing nanoparticles NF-DOX1-[HSA]MIP-NGs of Example 4. FIG. 25 shows the relationship between the concentration (MIP-NGs concentration (μg/mL)) and the cell viability (%) of the non-fluorescent drug-loaded HSA-recognizing nanoparticles NF-DOX2-[HSA]MIP-NGs of Example 5.

As shown in FIGS. 24 and 25, it was shown that the cell viability decreases with increasing concentration of the nanoparticles of the present invention. For example, when the non-fluorescent drug-loaded HSA-recognizing nanoparticles NF-DOX1-[HSA]MIP-NGs of Example 4 has a concentration of 100 μg/mL, the cell viability was found to be 64%, and when the non-fluorescent drug-loaded HSA-recognizing nanoparticles NF-DOX2-[HSA]MIP-NGs of Example 5 has a concentration of 100 μg/mL, the cell viability was found to be 7%. In both cases, each cell viability is low.

18-6. Summary

From the above results, it was revealed that the anticancer drug-loaded nanoparticles of the present invention showed toxicity to cells. On the other hand, since cytotoxicity was hardly observed in the nanoparticles that do not carry an anticancer agent, it is considered that cytotoxicity could be caused by carrying an anticancer agent. Therefore, it was demonstrated that the anticancer drug-loaded nanoparticle of the present invention is useful as a nanocarrier having an anti-cancer action.

Although preferred embodiments of the present invention are as described above, the present invention is not limited to the above-described embodiments, and various modifications are made without departing from the spirit of the present invention.

The invention claimed is:

1. An in vivo stealth nanoparticle to be used in intravascular delivery, wherein the in vivo stealth nanoparticle comprises:
   a molecularly imprinted polymer having external plasma protein recognition sites molecularly imprinted thereon by a plasma protein, wherein the molecularly imprinted polymer comprises a component derived from each of a functional monomer and a biocompatible monomer, wherein the functional monomer comprises a functional group capable of binding to the plasma protein and a polymerizable functional group, and wherein the molecularly imprinted polymer comprises 2-50 mol % of the biocompatible monomer polymerized into the polymer, and a drug component contained within in the molecularly imprinted polymer, wherein, when the in vivo stealth nanoparticle is delivered intravascularly, it binds plasma proteins to the external plasma protein recognition sites.

2. The in vivo stealth nanoparticle according to claim 1, wherein the plasma protein is albumin.

3. The in vivo stealth nanoparticle according to claim 1, wherein the biocompatible monomer is a zwitterionic compound.

4. The in vivo stealth nanoparticle according to claim 1, wherein the average particle diameter is 10 nm or more and 100 nm or less.

5. The in vivo stealth nanoparticle according to claim 1, further containing a signal group.

6. The in vivo stealth nanoparticle according to claim 1, wherein the drug component is a constituent derived from a drug monomer in which a polymerizable functional group is covalently bonded to the drug.

7. An in vivo stealth nanoparticle to be used in intravascular delivery, which is a molecularly imprinted polymer having a plasma protein recognition sites molecularly imprinted thereon by a plasma protein and containing a constituent derived from a biocompatible monomer, wherein the biocompatible polymer is phosphobetaine, wherein, when the in vivo stealth nanoparticle is delivered intravascularly, it binds plasma proteins to the plasma protein recognition sites so that the molecularly imprinted polymer is enclosed by the plasma proteins.

8. A method of protecting a drug from an immune response in a subject, the method comprising:

providing an in vivo nanoparticle according to claim 1, wherein the drug is the drug component contained within in the molecularly imprinted polymer, and administering the in vivo nanoparticle to the subject, wherein the in vitro nanoparticle binds plasma proteins in blood of the subject to the external plasma protein recognition sites so that the molecularly imprinted polymer nanoparticle and the drug component contained therein evade immune responses in the subject.

* * * * *